United States Patent
Gordon et al.

(10) Patent No.: US 11,021,812 B2
(45) Date of Patent: *Jun. 1, 2021

(54) FILAMENTS COMPRISING AN INGESTIBLE ACTIVE AGENT NONWOVEN WEBS AND METHODS FOR MAKING SAME

(75) Inventors: Gregory Charles Gordon, Loveland, OH (US); Robert Wayne Glenn, Jr., Liberty Township, OH (US); Mark Robert Sivik, Mason, OH (US); Mark Ryan Richards, Hamilton, OH (US); Stephen Wayne Heinzman, Cincinnati, OH (US); Michael David James, Cincinnati, OH (US); Geoffrey William Reynolds, Montgomery, OH (US); Paul Dennis Trokhan, Hamilton, OH (US); Paul Thomas Weisman, Cincinnati, OH (US); Steven Ray Gilbert, Fairfield, OH (US); Trevor John Darcy, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/229,818

(22) Filed: Sep. 12, 2011

(65) Prior Publication Data

US 2012/0027838 A1 Feb. 2, 2012

Related U.S. Application Data

(63) Continuation of application No. PCT/US2011/042662, filed on Jun. 30, 2011.

(60) Provisional application No. 61/361,135, filed on Jul. 2, 2010.

(51) Int. Cl.
| | | |
|---|---|---|
| *D01F 9/00* | (2006.01) | |
| *D01F 1/10* | (2006.01) | |
| *D01F 4/00* | (2006.01) | |
| *D04H 3/009* | (2012.01) | |
| *A61K 31/192* | (2006.01) | |
| *D04H 3/00* | (2012.01) | |
| *A61K 9/00* | (2006.01) | |
| *D01F 6/14* | (2006.01) | |
| *D04H 1/425* | (2012.01) | |
| *D04H 1/4258* | (2012.01) | |
| *D04H 1/4266* | (2012.01) | |

(52) U.S. Cl.
CPC .............. *D01F 9/00* (2013.01); *A61K 9/0056* (2013.01); *A61K 31/192* (2013.01); *D01F 1/10* (2013.01); *D01F 4/00* (2013.01); *D01F 6/14* (2013.01); *D04H 1/425* (2013.01); *D04H 1/4258* (2013.01); *D04H 1/4266* (2013.01); *D04H 3/00* (2013.01); *D04H 3/009* (2013.01)

(58) Field of Classification Search
CPC ..... D01F 9/00; D01F 1/10; D01F 4/00; D01F 6/14; D04H 3/009; D04H 3/00; D04H 1/425; D04H 1/4258; D04H 1/4266; A61K 31/192; A61K 9/0056; A61K 9/70; A61K 47/30; A61K 47/36; D01H 1/00
See application file for complete search history.

(56) References Cited

U.S. PATENT DOCUMENTS

| | | |
|---|---|---|
| 3,293,718 A | 12/1966 | Thomas |
| 3,859,125 A | 1/1975 | Miller et al. |
| 3,904,543 A | 9/1975 | Knighten |
| 4,286,016 A | 8/1981 | Dimond et al. |
| 4,287,219 A | 9/1981 | Fabre |
| 4,315,965 A | 2/1982 | Mason et al. |
| 4,342,813 A | 8/1982 | Erickson |
| 4,349,531 A | 9/1982 | Mlodozeniec et al. |
| 4,377,615 A | 3/1983 | Suzuki et al. |
| 4,415,617 A | 11/1983 | D'Elia |
| 4,639,390 A | 1/1987 | Shoji |
| 4,892,758 A | 1/1990 | Serbiak et al. |
| 5,230,853 A | 7/1993 | Colegrove et al. |
| 5,470,424 A | 11/1995 | Isaac et al. |
| 5,518,730 A | 5/1996 | Fuisz |
| 5,520,924 A | 5/1996 | Chapman et al. |
| 5,538,735 A | 7/1996 | Ahn |
| 5,780,418 A | 7/1998 | Niinaka et al. |
| 5,879,493 A | 3/1999 | Johnson et al. |
| 5,914,124 A | 6/1999 | Mahoney et al. |
| 6,207,274 B1 | 3/2001 | Ferenc et al. |
| 6,319,510 B1 | 11/2001 | Yates |
| 6,420,625 B1 | 7/2002 | Jones et al. |
| 6,552,123 B1 | 4/2003 | Katayama et al. |
| 7,094,744 B1 | 8/2006 | Kobayashi et al. |
| 7,115,551 B2 | 10/2006 | Hasenorhrl et al. |
| 7,196,026 B2 | 3/2007 | Di Luccio et al. |
| RE39,557 E | 4/2007 | Moe |

(Continued)

FOREIGN PATENT DOCUMENTS

| | | |
|---|---|---|
| EP | 1 887 036 A2 | 2/2008 |
| JP | 3040879 A | 2/1991 |

(Continued)

OTHER PUBLICATIONS

Russian International Search Report dated Dec. 25, 2017—2 pages.
All Office Actions in U.S. Appl. No. 13/229,791, U.S. Appl. No. 13/229,812, U.S. Appl. No. 13/229,825, U.S. Appl. No. 13/229,833, U.S. Appl. No. 13/229,838, U.S. Appl. No. 13/229,845, U.S. Appl. No. 13/229,852.

(Continued)

*Primary Examiner* — Robert S Cabral
(74) *Attorney, Agent, or Firm* — C. Brant Cook

(57) ABSTRACT

Filaments containing a filament-forming material and an additive, such as an ingestible active agent, nonwoven webs, and methods for making such filaments are provided.

27 Claims, 3 Drawing Sheets

(56) References Cited

U.S. PATENT DOCUMENTS

| | | |
|---|---|---|
| 7,226,899 B2 | 6/2007 | Cole et al. |
| 7,285,520 B2 | 10/2007 | Krzysik et al. |
| 7,387,787 B2 | 6/2008 | Fox |
| 7,407,669 B2 | 8/2008 | Leung et al. |
| 7,429,273 B2 | 9/2008 | DeDominicis et al. |
| 7,446,084 B2 | 11/2008 | Barthel et al. |
| 7,491,407 B2 | 2/2009 | Pourdeyhimi et al. |
| 7,507,698 B2 | 3/2009 | Franzolin et al. |
| 7,856,989 B2 | 12/2010 | Karles et al. |
| 2001/0037851 A1 | 11/2001 | Mortellite et al. |
| 2002/0161088 A1 | 10/2002 | Kochvar et al. |
| 2002/0173213 A1 | 11/2002 | Chu et al. |
| 2003/0017208 A1 | 1/2003 | Ignatious et al. |
| 2003/0045446 A1 | 3/2003 | Dihora et al. |
| 2003/0166495 A1 | 9/2003 | Wang et al. |
| 2003/0185872 A1 | 10/2003 | Kochinke |
| 2004/0170836 A1 | 9/2004 | Bond et al. |
| 2005/0003048 A1 | 1/2005 | Pearce et al. |
| 2005/0003991 A1 | 1/2005 | MacQuarrie |
| 2005/0008776 A1 | 1/2005 | Chhabra et al. |
| 2005/0136112 A1 | 6/2005 | Gonzales et al. |
| 2005/0136780 A1 | 6/2005 | Clark et al. |
| 2005/0209574 A1 | 9/2005 | Boehringer et al. |
| 2005/0281757 A1 | 12/2005 | Ibrahim et al. |
| 2006/0013869 A1 | 1/2006 | Ignatious et al. |
| 2006/0083784 A1 | 4/2006 | Ignatious et al. |
| 2006/0160453 A1 | 7/2006 | Suh |
| 2007/0054579 A1 | 3/2007 | Baker et al. |
| 2007/0259170 A1 | 11/2007 | Brown et al. |
| 2007/0298064 A1 | 12/2007 | Koslow |
| 2008/0220054 A1 | 9/2008 | Shastri et al. |
| 2008/0242572 A1 | 10/2008 | Icht et al. |
| 2009/0004254 A1 | 1/2009 | Maibach |
| 2009/0041820 A1 | 2/2009 | Wu et al. |
| 2009/0061719 A1 | 3/2009 | Shibutani et al. |
| 2009/0155326 A1* | 6/2009 | Mack .................. A61K 9/0051 424/402 |
| 2009/0181587 A1 | 7/2009 | Kang et al. |
| 2009/0249558 A1 | 10/2009 | Fileccia et al. |
| 2009/0285718 A1 | 11/2009 | Privitera et al. |
| 2010/0018641 A1* | 1/2010 | Branham et al. ........ 156/244.17 |
| 2010/0021517 A1 | 1/2010 | Ahlers et al. |
| 2010/0098745 A1 | 4/2010 | Staab |
| 2010/0166854 A1 | 7/2010 | Michniak-Kohn et al. |
| 2010/0266668 A1 | 10/2010 | Coffee et al. |
| 2011/0136719 A1 | 6/2011 | Jalbert et al. |
| 2011/0223381 A1 | 9/2011 | Mackey et al. |
| 2011/0301070 A1 | 12/2011 | Ochomogo et al. |
| 2012/0021026 A1 | 1/2012 | Glenn, Jr. et al. |
| 2012/0058100 A1 | 3/2012 | Shastri et al. |
| 2012/0172831 A1 | 7/2012 | Darcy et al. |

FOREIGN PATENT DOCUMENTS

| | | |
|---|---|---|
| JP | 3101618 A | 4/1991 |
| JP | 10158700 A | 6/1998 |
| JP | 2000169896 A | 6/2000 |
| WO | WO 99/57155 | 11/1999 |
| WO | WO 2000/013680 A2 | 3/2000 |
| WO | WO 01/25322 A1 | 4/2001 |
| WO | WO 2001/54667 A1 | 8/2001 |
| WO | WO 03/060007 A1 | 7/2003 |
| WO | WO 2006/106514 A2 | 10/2006 |
| WO | WO 2007/089259 A1 | 8/2007 |
| WO | WO 2007/093558 A3 | 1/2008 |
| WO | WO 2009/022761 A1 | 2/2009 |

OTHER PUBLICATIONS

Makadia, et al., "Poly Lactic-co-Glycolic Acid (PLGA) as Biodegradable Controlled Drug Delivery Carrier", *Polymers*, 3, pp. 1377-1397 (2011).

Wang, et al., "A Novel Controlled Release Drug Delivery System for Multiple Drugs Based on Electrospun Nanofibers Containing Nanoparticles", *Journal of Pharmaceutical Sciences*, vol. 99, No. 12 (Dec. 2010).

All Office Actions in U.S. Appl. No. 13/229,791, U.S. Appl. No. 13/229,812, U.S. Appl. No. 13/229,818, U.S. Appl. No. 13/229,825, U.S. Appl. No. 13/229,833, U.S. Appl. No. 13/229,838, U.S. Appl. No. 13/229,845, U.S. Appl. No. 13/229,852.

International Search Report dated Nov. 7, 2011.

U.S. Appl. No. 13/229,812, filed Sep. 12, 2011, Gordon, et al.

\* cited by examiner

FILAMENTS COMPRISING AN INGESTIBLE ACTIVE AGENT NONWOVEN WEBS AND METHODS FOR MAKING SAME

CROSS REFERENCE TO RELATED APPLICATION

This application is a continuation application of prior copending International Application No. PCT/US2011/042662, filed Jun. 30, 2011, designating the U.S., which claims the benefit of U.S. Provisional Application No. 61/361,135, filed Jul. 2, 2010.

FIELD OF THE INVENTION

The present invention relates to filaments and more particularly to filaments that comprise a filament-forming material and an additive, such as an ingestible active agent, nonwoven webs employing the filaments, and methods for making such filaments.

BACKGROUND OF THE INVENTION

Delivery of ingestible active agents by a substrate; namely a film is known in the art, especially for mouthwash, teeth whitening agents, and/or breath freshening purposes. For example, it is known to incorporate essential oils such as thymol, methyl salicylate, eucalyptol and/or menthol into a film to provide an antiseptic oral composition. However, films and processes for making films do not offer the flexibility and rates of production that filaments and/or nonwoven webs comprising such filaments offer.

Another example of a prior art execution is the use of electro spun dissolvable polysaccharide fibers that include a flavoring agent which can be incorporated into a cigarette to deliver flavoring as the fibers dissolve under moist air conditions produced by the user during smoking of the cigarette. The flavorings are present in the dissolvable fibers at less than or equal to 10% by weight of the fiber.

In addition, there are substrates/webs that are produced from thermoplastic polymers containing Lastly, as shown in prior art FIGS. 1 and 2, there are known nonwoven substrates 10 that are made of dissolvable fibers 12 wherein the nonwoven substrates 10 are coated and/or impregnated with an additive 14, such as a skin care benefit agent, rather than the additive 14 being present in the dissolvable fibers 12.

Even in light of the state of the art, there exists a need for a filament that comprises one or more filament-forming materials and one or more ingestible active agents that are releasable from the filament upon ingesting by an animal or in other words when the filament is exposed to conditions of intended use wherein the total level of the one or more filament-forming materials present in the filament is less than 80% by weight on a dry filament basis and the total level of the one or more active agents present in the filament is greater than 20% by weight on a dry filament basis. Such a filament would be suitable for carrying and/or delivering the active agents in various applications. Further, there is a desire to produce a filament that has a greater level of additive, for example an active agent, than the filament-forming material, for example a polymer in order to optimize the delivery of the active agent with minimal cost and relatively faster rate of delivery compared to filaments that have a greater level of filament-forming material than its additive.

It is also desirable to incorporate active agents into filaments that otherwise are incompatible with carrier substrates rising to separation from the substrate. The present invention allows normally incompatible active agents to be incorporated into the filament.

Many personal health care products in the market today are sold containing water. The water in the formula adds to the weight and size of the products and translates into greater shipping and storage costs. Additionally, these types of products also have disadvantages in terms of packaging, storage, transportation, and convenience of use. It can also be difficult to control the dosing of liquid personal health care products. Moreover, the presence of water in personal health care products increases susceptibility to degradation of water unstable ingredients and promotes negative interactions between two or more incompatible materials in an article.

Some personal health care products are swallowable and sold as capsules, pills, caplets, and tablets and consumers need a drink, such as water, to consume the product. It can be inconvenient for a consumer to find a drink to consume a personal health care product in this form. Other personal health care products are chewable and sold as tablets. These chewable tablets do not require a drink for consumption. However, they are not durable and tend to break when the consumer transports them and often have a chalky flavor. Furthermore, pediatric and geriatric patients have difficulty swallowing larger oral dosage forms.

Some personal health care products are available in a dissolvable strip. However, these strips have a low loading capacity which limits the variety and amount of personal health care actives that can be added to the dosage form. Furthermore, these strips and the processes for making the strips do not offer the flexibility and rates of production that personal health care articles comprising one or more filaments offer.

Therefore, a need exists for personal health care articles that do not contain a liquid, can be consumed by the consumer without a drink, are durable during transport, and can contain broad ranges of health care actives and aesthetic agents, which includes higher levels of health care actives than are currently available in dissolvable strips. The filaments and personal health care articles of this invention can be delivered to the consumer in need via the oral cavity, mouth, throat, nasal passage, rectum, vagina, skin, eyes, ears and combinations thereof. In one embodiment, the filaments and personal health care articles of this invention interact with the moisture in the oral cavity or mouth to disintegrate and release one or more health care actives that are then consumed by the consumer.

Accordingly, there exists a need for novel filaments that comprise a filament-forming material and an additive, for example an ingestible active agent that is releasable from the filament and methods for making such filaments.

SUMMARY OF THE INVENTION

The present invention fulfills the need described above by providing a filament comprising a filament-forming material and an additive that is releasable and/or release from the filament for example when the filament is exposed to condition of intended use.

In one example of the present invention, a filament comprising one or more filament-forming materials and one or more ingestible active agents that are releasable and/or released from the filament upon ingesting by an animal, wherein the total level of the filament-forming materials present in the filament is less than 80% by weight on a dry filament basis and the total level of the active agents present in the filament is greater than 20% by weight on a dry filament basis, is provided.

In another example of the present invention, a filament-forming composition suitable for producing filaments of the present invention, for example by a spinning process, the filament-forming composition comprises from about 5% to about 70% by weight of one or more filament-forming materials, from about 5% to about 70% by weight of one or more active agents, and from about 30% to about 70% by weight of one or more polar solvents (such as water) is provided.

In yet another example of the present invention, a filament-forming composition suitable for producing filaments of the present invention, for example by a spinning process, the filament-forming composition comprising about 5% to about 70% by weight of one or more active agents and from about 30% to about 70% by weight of one or more polar solvents (such as water) is provided.

In still another example of the present invention, a filament-forming composition suitable for producing filaments of the present invention, for example by a spinning process, the filament-forming composition comprising a total level of one or more filament-forming materials, a total level of one or more active agents, and one or more polar solvents (such as water) such that a filament produced from the filament-forming composition comprises less than 80% by weight on a dry filament basis of the one or more filament materials and greater than 20% by weight of a dry filament basis of the one or more ingestible active agents and optionally, less than 20% by weight of water, is provided.

In even still yet another example of the present invention, a nonwoven web comprising one or more filaments according to the present invention, is provided.

In another example of the present invention, a method for making a filament, the method comprises the steps of:

a. providing a filament-forming composition comprising one or more filament-forming materials and one or more active agents;

b. spinning the filament-forming composition into one or more filaments comprising the one or more filament-forming materials and the one or more active agents that are releasable and/or released from the filament upon ingesting by an animal, wherein the total level of the filament-forming materials present in the filament is less than 80% by weight on a dry filament basis and the total level of the active agents present in the filament is greater than 20% by weight on a dry filament basis, is provided.

Even though the examples provided herein refer to one or more filaments, fibers made from the filaments of the present invention, such as by cutting a filament into fibers, and nonwoven webs comprising such fibers, alone or in combination with one or more filaments of the present invention are also within the scope of the present invention.

Accordingly, the present invention provides filaments and/or fibers comprising one or more additives, such as active agents, nonwoven webs containing such filaments and/or fibers, and a method for making such filaments and/or fibers.

DETAILED DESCRIPTION OF THE INVENTION

Definitions

"Filament" as used herein means an elongate particulate having a length greatly exceeding its diameter, i.e. a length to diameter ratio of at least about 10.

The filaments of the present invention may be spun from filament-forming compositions via suitable spinning processes operations, such as meltblowing and/or spunbonding.

The filaments of the present invention may be monocomponent and/or multicomponent. For example, the filaments may comprise bicomponent filaments. The bicomponent filaments may be in any form, such as side-by-side, core and sheath, islands-in-the-sea and the like.

The filaments of the present invention exhibit a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers (which are less than 5.08 cm in length). Non-limiting examples of filaments include meltblown and/or spunbond filaments.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" as used herein means a composition that is suitable for making a filament of the present invention such as by meltblowing and/or spunbonding. The filament-forming composition comprises one or more filament-forming materials that exhibit properties that make them suitable for spinning into a filament. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed.

Figure 1:
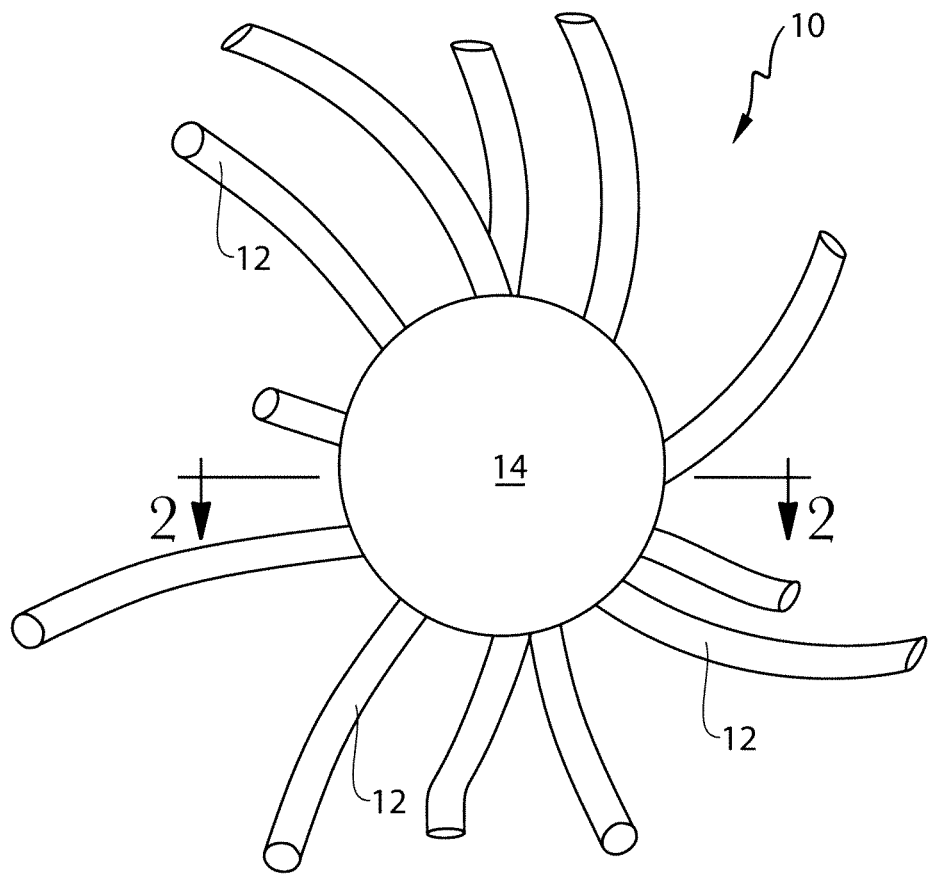
FIG. 1 is a schematic representation of a prior art nonwoven substrate made of dissolvable fibers that is coated with an additive.
Figure 2:
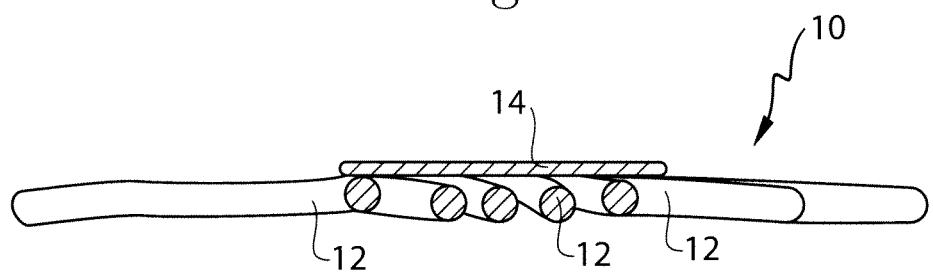
FIG. 2 is a cross-sectional view of FIG. 1 taken along line 2-2 of FIG. 1.
Figure 3:
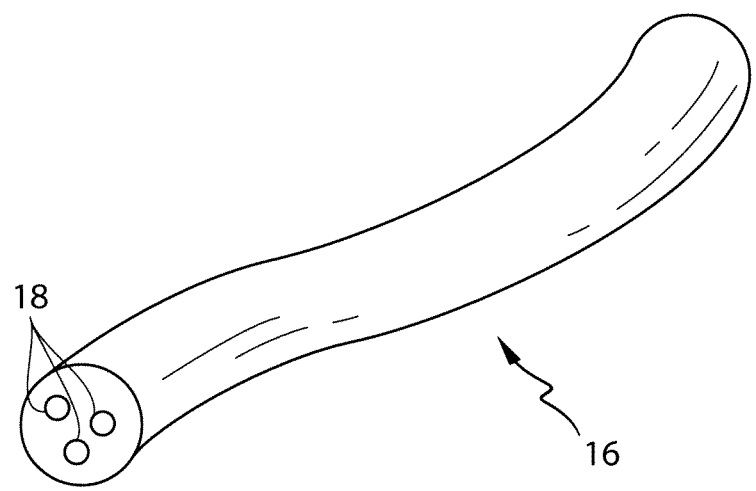
FIG. 3 is a schematic representation of a filament according to the present invention.

In one example as shown in FIG. 3 a filament 16 of the present invention made from a filament-forming composition of the present invention is such that one or more additives 18, for example one or more active agents, may be present in the filament rather than on the filament, such as a coating as shown in prior art FIGS. 1 and 2. The total level of filament-forming materials and total level of active agents present in the filament-forming composition may be any suitable amount so long as the filaments of the present invention are produced therefrom.

In one example, one or more additives, such as active agents, may be present in the filament and one or more additional additives, such as active agents, may be present on a surface of the filament. In another example, a filament of the present invention may comprise one or more additives, such as active agents, that are present in the filament when originally made, but then bloom to a surface of the filament prior to and/or when exposed to conditions of intended use of the filament.

"Filament-forming material" as used herein means a material, such as a polymer or monomers capable of producing a polymer that exhibits properties suitable for making a filament. In one example, the filament-forming material comprises one or more substituted polymers such as an anionic, cationic, zwitterionic, and/or nonionic polymer. In another example, the polymer may comprise a hydroxyl polymer, such as a polyvinyl alcohol and/or a polysaccharide, such as starch and/or a starch derivative, such as an ethoxylated starch and/or acid-thinned starch. In another example, the polymer may comprise polyethylenes and/or terephthalates. In yet another example, the filament-forming material is a polar solvent-soluble material.

"Additive" as used herein means any material present in the filament of the present invention that is not a filament-forming material. In one example, an additive comprises an active agent. In another example, an additive comprises a processing aid. In still another example, an additive comprises a filler. In one example, an additive comprises any material present in the filament that its absence from the filament would not result in the filament losing its filament structure, in other words, its absence does not result in the filament losing its solid form. In another example, an additive, for example an active agent, comprises a non-polymer material.

In another example, an additive comprises a plasticizer for the filament. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, urea, sorbitol, xylitol, maltitol, sugars, ethylene bisformamide, amino acids, and mixtures thereof.

In another example, an additive comprises a crosslinking agent suitable for crosslinking one or more of the filament-forming materials present in the filaments of the present invention. In one example, the crosslinking agent comprises a crosslinking agent capable of crosslinking hydroxyl polymers together, for example via the hydroxyl polymers hydroxyl moieties. Non-limiting examples of suitable crosslinking agents include imidazolidinones, polycarboxylic acids and mixtures thereof. In one example, the crosslinking agent comprises a urea glyoxal adduct crosslinking agent, for example a dihydroxyimidazolidinone, such as dihydroxyethylene urea ("DHEU"). A crosslinking agent can be present in the filament-forming composition and/or filament of the present invention to control the filament's solubility and/or dissolution in a solvent, such as a polar solvent.

In another example, an additive comprises a rheology modifier, such as a shear modifier and/or an extensional modifier. Non-limiting examples of rheology modifiers include but not limited to polyacrylamide, polyurethanes and polyacrylates that may be used in the filaments of the present invention. Non-limiting examples of rheology modifiers are commercially available from The Dow Chemical Company (Midland, Mich.).

In yet another example, an additive comprises one or more colors and/or dyes that are incorporated into the filaments of the present invention to provide a visual signal when the filaments are exposed to conditions of intended use and/or when an active agent is released from the filaments and/or when the filament's morphology changes.

In still yet another example, an additive comprises one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants are applied to the filament, in other words, after the filament is formed. In one example, one or more release agents/lubricants are applied to the filament prior to collecting the filaments on a collection device to form a nonwoven. In another example, one or more release agents/lubricants are applied to a nonwoven web formed from the filaments of the present invention prior to contacting one or more nonwoven webs, such as in a stack of nonwoven webs. In yet another example, one or more release agents/lubricants are applied to the filament of the present invention and/or nonwoven comprising the filament prior to the filament and/or nonwoven contacting a surface, such as a surface of equipment used in a processing system so as to facilitate removal of the filament and/or nonwoven web and/or to avoid layers of filaments and/or nonwoven webs of the present invention sticking to one another, even inadvertently. In one example, the release agents/lubricants comprise particulates.

In even still yet another example, an additive comprises one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a filament of the present invention is exposed to when the filament is used for one or more of its designed purposes. For example, if a filament and/or a nonwoven web comprising a filament is designed to be used in a washing machine for laundry care purposes, the conditions of intended use will include those temperature, chemical, physical and/or mechanical conditions present in a washing machine, including any wash water, during a laundry washing operation. In another example, if a filament and/or a nonwoven web comprising a filament is designed to be used by a human as a shampoo for hair care purposes, the conditions of intended use will include those temperature, chemical, physical and/or mechanical conditions present during the shampooing of the human's hair. Likewise, if a filament and/or nonwoven web comprising a filament is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a filament and/or nonwoven web comprising the filament of the present, such as when the filament is exposed to conditions of intended use of the filament and/or nonwoven web comprising the filament. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the filament containing the active agent, for example the filament may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

As used herein, the term "treat" or "treating" includes preventing, alleviating, ameliorating, inhibiting, or mitigating one or more health conditions. Non-limiting examples of health conditions can include respiratory conditions, gastrointestinal conditions, central nervous system conditions, pathogenic infections, nutritional deficiencies, and combinations thereof. In one example, the mammal treated may be a human and in another example that mammal can be a companion animal such as a dog, cat or horse.

As used herein, the term "prevent", "preventing" or "prevention" includes preventing one or more health care conditions or its associated symptoms from occurring in a mammal, for example when the mammal is predisposed to acquiring the symptoms of coughing, inhibiting the onset of coughing or its associated symptoms; and/or alleviating, reversing, or curing the coughing episode or its associated symptoms.

As used herein, the term "orally administering" and/or "administering" with respect to the human/mammal means that the human/mammal consumes or is directed to consume (whether by swallowing or any other means) one or more of the personal health care articles. The human/mammal may be directed to deliver the personal health care article to the site that the human/mammal intends to treat, for example, the oral mucosa. The human/mammal may be directed to consume the personal health care article, and such direction and or delivery may be that which instructs and/or informs the human that use of the personal health care article may provide a wellness benefit. The benefit can be instant, delayed or extended. For example, such direction may be oral direction (e.g., through oral instruction from, for example, a physician, pharmacist, or other health professional), radio or television media (e.g., advertisement), or written direction (e.g., through written direction from, for example, a physician, pharmacist, or other health professional (e.g., scripts), sales professional organization (e.g., through, for example, marketing brochures, pamphlets, or other instructive paraphernalia), written media (e.g., internet, electronic mail, or other computer-related media)), and/or packaging associated with the personal health care article (e.g., a label present on a delivery device holding the personal health care article). As used herein, "written" means through words, pictures, symbols, and/or other visible or tactile descriptors. Such information need not utilize the actual words used herein, for example, "respiratory", "symptom", or "mammal", but rather use of words, pictures, symbols, tactile means, and the like conveying the same or similar meaning are contemplated within the scope of this invention.

Health care active agents and aesthetic agents useful herein may be categorized or described herein by their health benefit and/or health conditions or their postulated mode of action or function. However, it is to be understood that the health care actives and aesthetic agents useful herein can, in some instances, provide more than one health benefit and/or health conditions or function or operate via more than one mode of action. Therefore, classifications herein are made for the sake of convenience and are not intended to limit an ingredient to the particularly stated function(s) or activities listed.

"Weight ratio" as used herein means the weight of filament-forming material (g or %) on a dry weight basis in the filament to the weight of additive (g or %) on a dry weight basis in the filament.

"Hydroxyl polymer" as used herein includes any hydroxyl-containing polymer that can be incorporated into a filament of the present invention, for example as a filament-forming material. In one example, the hydroxyl polymer of the present invention includes greater than 10% and/or greater than 20% and/or greater than 25% by weight hydroxyl moieties.

"Biodegradable" as used herein means, with respect to a material, such as a filament as a whole and/or a polymer within a filament, such as a filament-forming material, that the filament and/or polymer is capable of undergoing and/or does undergo physical, chemical, thermal and/or biological degradation in a municipal solid waste composting facility such that at least 5% and/or at least 7% and/or at least 10% of the original filament and/or polymer is converted into carbon dioxide after 30 days as measured according to the OECD (1992) Guideline for the Testing of Chemicals 301B; Ready Biodegradability—$CO_2$ Evolution (Modified Sturm Test) Test incorporated herein by reference.

"Non-biodegradable" as used herein means, with respect to a material, such as a filament as a whole and/or a polymer within a filament, such as a filament-forming material, that the filament and/or polymer is not capable of undergoing physical, chemical, thermal and/or biological degradation in a municipal solid waste composting facility such that at least 5% of the original filament and/or polymer is converted into carbon dioxide after 30 days as measured according to the OECD (1992) Guideline for the Testing of Chemicals 301B; Ready Biodegradability—$CO_2$ Evolution (Modified Sturm Test) Test incorporated herein by reference.

"Non-thermoplastic" as used herein means, with respect to a material, such as a filament as a whole and/or a polymer within a filament, such as a filament-forming material, that the filament and/or polymer exhibits no melting point and/or softening point, which allows it to flow under pressure, in the absence of a plasticizer, such as water, glycerin, sorbitol, urea and the like.

"Non-thermoplastic, biodegradable filament" as used herein means a filament that exhibits the properties of being biodegradable and non-thermoplastic as defined above.

"Non-thermoplastic, non-biodegradable filament" as used herein means a filament that exhibits the properties of being non-biodegradable and non-thermoplastic as defined above.

"Thermoplastic" as used herein means, with respect to a material, such as a filament as a whole and/or a polymer within a filament, such as a filament-forming material, that the filament and/or polymer exhibits a melting point and/or softening point at a certain temperature, which allows it to flow under pressure, in the absence of a plasticizer "Thermoplastic, biodegradable filament" as used herein means a filament that exhibits the properties of being biodegradable and thermoplastic as defined above.

"Thermoplastic, non-biodegradable filament" as used herein means a filament that exhibits the properties of being non-biodegradable and thermoplastic as defined above.

"Non-cellulose-containing" as used herein means that less than 5% and/or less than 3% and/or less than 1% and/or less than 0.1% and/or 0% by weight of cellulose polymer, cellulose derivative polymer and/or cellulose copolymer is present in filament. In one example, "non-cellulose-containing" means that less than 5% and/or less than 3% and/or less than 1% and/or less than 0.1% and/or 0% by weight of cellulose polymer is present in filament.

"Polar solvent-soluble material" as used herein means a material that is miscible in a polar solvent. In one example, a polar solvent-soluble material is miscible in alcohol and/or water. In other words, a polar solvent-soluble material is a material that is capable of forming a stable (does not phase separate for greater than 5 minutes) homogeneous solution with a polar solvent, such as alcohol and/or water at ambient conditions.

"Alcohol-soluble material" as used herein means a material that is miscible in alcohol. In other words, a material that is capable of forming a stable (does not phase separate for greater than 5 minutes) homogeneous solution with alcohol at ambient conditions.

"Water-soluble material" as used herein means a material that is miscible in water. In other words, a material that is capable of forming a stable (does not separate for greater than 5 minutes) homogeneous solution with water at ambient conditions.

"Non-polar solvent-soluble material" as used herein means a material that is miscible in a non-polar solvent. In other words, a non-polar solvent-soluble material is a material that is capable of forming a stable (does not phase separate for greater than 5 minutes) homogeneous solution with a non-polar solvent.

"Ambient conditions" as used herein means 73° F.±4° F. (about 23° C.±2.2° C.) and a relative humidity of 50%±10%.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Length" as used herein, with respect to a filament, means the length along the longest axis of the filament from one terminus to the other terminus. If a filament has a kink, curl or curves in it, then the length is the length along the entire path of the filament.

"Diameter" as used herein, with respect to a filament, is measured according to the Diameter Test Method described herein. In one example, a filament of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"Triggering condition" as used herein in one example means anything, as an act or event, that serves as a stimulus and initiates or precipitates a change in the filament, such as a loss or altering of the filament's physical structure and/or a release of an additive, such as an active agent. In another example, the triggering condition may be present in an environment, such as water, when a filament and/or nonwoven web and/or film of the present invention is added to the water. In other words, nothing changes in the water except for the fact that the filament and/or nonwoven and/or film of the present invention is added to the water.

"Morphology changes" as used herein with respect to a filament's morphology changing means that the filament experiences a change in its physical structure. Non-limiting examples of morphology changes for a filament of the present invention include dissolution, melting, swelling, shrinking, breaking into pieces, exploding, lengthening, shortening, and combinations thereof. Non-limiting examples of morphology changes for a filament of the present invention include dissolution, melting, swelling, shrinking, breaking into pieces, exploding, lengthening, shortening, and combinations thereof. The filaments of the present invention may completely or substantially lose their filament physical structure or they may have their morphology changed or they may retain or substantially retain their filament physical structure as they are exposed to conditions of intended use.

"By weight on a dry filament basis" means that the weight of the filament measured immediately after the filament has been conditioned in a conditioned room at a temperature of 73° F.±4° F. (about 23° C.±2.2° C.) and a relative humidity of 50%±10% for 2 hours. In one example, "by weight on a dry filament basis" means that the filament comprises less than 20% and/or less than 15% and/or less than 10% and/or less than 7% and/or less than 5% and/or less than 3% and/or to 0% and/or to greater than 0% based on the weight of the filament of moisture, such as water, for example free water, as measured according to the Water Content Test Method described herein.

"Total level" as used herein, for example with respect to the total level of one or more active agents present in the filament, means the sum of the weights or weight percent of all of the subject materials, for example active agents. In other words, a filament may comprise 25% by weight on a dry filament basis of an anionic surfactant, 15% by weight on a dry filament basis of a nonionic surfactant, 10% by weight of a chelant, and 5% of a perfume so that the total level of active agents present in the filament is greater than 50%; namely 55% by weight on a dry filament basis.

"Web" as used herein means a collection of formed fibers and/or filaments, such as a fibrous structure, and/or a sheet formed of fibers and/or filaments, such as continuous filaments, of any nature or origin associated with one another. In one example, the web is a sheet that is formed via a spinning process, not a cast process.

"Nonwoven web" for purposes of the present invention as used herein and as defined generally by European Disposables and Nonwovens Association (EDANA) means a sheet of fibers and/or filaments, such as continuous filaments, of any nature or origin, that have been formed into a web by any means, and may be bonded together by any means, with the exception of weaving or knitting. Felts obtained by wet milling are not nonwoven webs. In one example, a nonwoven web according to the present invention means an orderly arrangement of filaments within a structure in order to perform a function. In one example, a nonwoven web of the present invention is an arrangement comprising a plurality of two or more and/or three or more filaments that are inter-entangled or otherwise associated with one another to form a nonwoven web. In one example, the nonwoven web of the present invention may comprise, in addition to the filaments of the present invention, one or more solid additives, such as particulates and/or fibers.

"Particulates" as used herein means granular substances and/or powders.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Personal Health Care Article

A personal health care article according to the present invention comprises one or more filaments and/or a nonwoven web comprising one or more filaments of the present invention. The personal health care article can be administered directly to a mammal or incorporated into a device. The use of such a personal health care article allows for easy portability and the ability to better control dosing. Once disintegrated or dissolved, the personal health care article can be consumed by to the consumer.

The personal health care article can also be delivered via a water insoluble implement or device. For instance, the personal health care article may be attached or glued by some mechanism to an applicator to facilitate application to the oral cavity, mouth, throat, nasal passage, rectum, vagina, skin i.e., a comb, rag, wand, or any other conceivable water-insoluble applicator. In an example, the personal health care article is placed into a liquid, such as water, disintegrated and then administered to the mammal.

In an example, the personal health care article of the present invention has a basis weight of from about 20 grams per square meter ($g/m^2$) to about 1000 $g/m^2$ and/or from about 25 $g/m^2$ to about 500 $g/m^2$ and/or from about 40 $g/m^2$ to about 250 $g/m^2$ and/or from about 50 $g/m^2$ to about 100 $g/m^2$.

In an example, the personal health care article of the present invention can be a flat article in the form of a pad, strip, tape, or tablet having a thickness of from about 0.05 millimeter (mm) to about 20 mm and/or from about 0.05 mm to about 10 mm and/or from about 0.05 mm to about 5 mm and/or from about 0.5 mm to about 1 mm and/or from about 0.05 mm to about 0.5 mm and/or from about 0.05 mm to about 0.25 mm and/or from about 0.05 mm to about 0.1 mm as measured by the Thickness Test Method described herein. In another example, the personal health care article can be formed into a cylindrical shape (e.g. by rolling) having a length from about 0.5 centimeter (cm) to about 10 cm and/or from about 1 cm to about 5 cm and/or from about 1.5 cm to about 3 cm. In another example the personal health care article can be a rectangular prism including a cube wherein the longest sides of the rectangular prism has a length from about 5 mm to 20 mm and/or from about 10 mm to 15 mm and/or from about 5 mm to about 10 mm as measured by the Thickness Test Method described herein.

In an example, the personal health care article is in the form of one or more flat sheets or pads of an adequate size to be able to be handled easily by the user. In another example, the flat sheet or pad contains one dose of one or more health care actives that can provide one or more health benefits and/or treat one or more health conditions. The personal health care article may have a square, rectangle or disc shape or any other suitable shape. The personal health care article can also be in the form of a continuous strip including delivery on a tape-like roll dispenser with individual portions dispensed via perforations and/or a cutting mechanism.

The personal health care articles of the present invention can be formed by one or more nonwoven webs. The nonwoven web may be formed by one or more filaments. In another example, the personal health care article may comprise two or more layers wherein at least one of the layers comprises a nonwoven web. In another example, the personal health care article comprises two or more layers wherein each of the layers comprises a nonwoven web. In another example, the personal health care article comprises a first nonwoven web and a second nonwoven web wherein the first nonwoven web comprises a health care active and the second nonwoven web comprises an aesthetic agent.

In an example, the nonwoven web contains more than one filament. In another example, the nonwoven web comprises a first filament and a second filament both comprising a health care active and the health care active can be the same health care active or different health care actives. In another example, the nonwoven web comprises a first filament comprising an immediate delivery health care active and a second filament comprising an extended delivery, a delayed delivery, and/or a targeted delivery health care active. In another example, the nonwoven web comprises a first filament and a second filament wherein the first filament comprises one or more health care actives and the second filament comprises one or more aesthetic agents. In another example, the nonwoven web comprises a first filament, a second filament, and a third filament, wherein each filament comprises a different health care active.

In an example, the nonwoven web or personal health care article comprises a plurality of identical or substantially identical, from a compositional perspective, filaments according to the present invention. In another example, the nonwoven web or personal health care article may comprise two or more different filaments according to the present invention. Non-limiting examples of differences in the filaments may be physical differences such as differences in diameter, length, texture, shape, rigidness, elasticity, and the like; chemical differences such as crosslinking level, solubility, melting point, glass transition temperature (Tg), backbone material, color, amount of health care active, amount of backbone material, presence of a coating composition on the filament, chemical composition of the health care active including whether the health care active is immediate delivery, delayed delivery, extended delivery, or targeted delivery, and the like; differences in whether the filament loses its physical structure when the filament is exposed to conditions of intended use; differences in whether the filament's morphology changes when the filament is exposed to conditions of intended use; and differences in when and where the benefit from the health care active is experienced. In one example, two or more filaments within the personal health care article or nonwoven web may comprise the same backbone material, but have different health care actives.

In an example, the personal health care article or nonwoven web comprises two or more filaments wherein the filaments release the health care actives at different rates. The different rates may be caused by the filaments being positioned at an external surface of the nonwoven web.

In an example, the personal health care article or nonwoven web comprises two or more active agents that are generally considered incompatible with one another in a liquid formulation, for example simethicone and calcium carbonate. Health care actives are incompatible with one another, if when they are in the same composition, at least one of the health care actives has a significant reduction in efficacy, stability, or bioavailability.

In another example, the personal health care article or nonwoven web may exhibit different regions, such as different regions of basis weight, density and/or caliper. In an example, the personal health care article or nonwoven web may comprise discrete regions of filaments that differ from other parts of the nonwoven web.

The personal health care article or the nonwoven web may comprise one or more textured, dimpled or otherwise topographically patterned surfaces including letters, logos or figures. The textured personal health care article can result from the shape of the filament or the nonwoven web, in that the outermost surface of the article contains portions that are raised with respect to other areas of the surface. The raised portions can result from the formed shape of the personal health care article, for example the nonwoven web can be formed in a dimpled or waffle pattern. The raised portions can also be the result of creping processes, imprinted coatings, embossing patterns, or the result of the physical form of the article itself.

In an example, the nonwoven web of the present invention may be pressed into a film to form the personal health care article; this can be done by applying a compressive force and/or heating the nonwoven web to convert the nonwoven web into a film. The film would comprise the health care actives that were present in the filaments of the present invention. The nonwoven web may be completely converted into a film or parts of the nonwoven web may remain in the form of a film after partial conversion of the nonwoven web into the film. In yet another example, the personal health care article may constitute one or more nonwoven webs wherein at least one of the nonwoven webs has been pressed into a film. In another example, the personal health care article comprises two or more nonwoven webs that have been pressed into a film.

In another example, the nonwoven web can be rolled, compressed, cut, or stacked to form a three dimensional personal health care article. For instance, the nonwoven web may be compressed into a pill or tablet, rolled into a cylinder, or compressed or stacked into a rectangular prism to form the personal health care article.

In another example, the personal health care article may constitute one or more layers of nonwoven webs which are optionally bonded together via a bonding means (including heat, moisture, ultrasonic, pressure etc.).

In another example, the personal health care article or nonwoven web can be perforated with holes or channels penetrating into or through the personal health care article or nonwoven web. These perforations can be formed as part of making the nonwoven web or personal health care article via spikes extended from the surface of an adjacent belt, drum, roller or other surface. Alternatively, these perforations can be formed after forming the nonwoven web or personal health care article by a process of poking or sticking the porous solids with pins, needles or other sharp objects.

Filament

The filament of the present invention comprises one or more filament-forming materials and one or more ingestible active agents that are releasable from the filament, such as when the filament is exposed to conditions of intended use, wherein the total level of the one or more filament-forming materials present in the filament is less than 80% by weight on a dry filament basis and the total level of the one or more active agents present in the filament is greater than 20% by weight on a dry filament basis, is provided.

In one example, the filament of the present invention comprises one or more filament-forming materials and one or more active agents wherein the total level of filament-forming materials present in the filament is from about 5% to less than 80% by weight on a dry filament basis and the total level of active agents present in the filament is greater than 20% to about 95% by weight on a dry filament basis.

In one example, the filament of the present invention comprises at least 10% and/or at least 15% and/or at least 20% and/or less than 80% and/or less than 65% and/or less than 60% and/or less than 55% and/or less than 50% and/or less than 45% and/or less than 40% by weight on a dry filament basis of the filament-forming materials and greater than 20% and/or at least 35% and/or at least 40% and/or at least 45% and/or at least 50% and/or at least 60% and/or at least 65% and/or less than 95% and/or less than 90% and/or less than 85% and/or less than 80% and/or less than 75% by weight on a dry filament basis of active agents.

In another example, the one or more filament-forming materials and active agents are present in the filament at a weight ratio of total level of filament-forming materials to active agents of less than 4.0 and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In still another example, the filament of the present invention comprises from about 5% to less than 80% by weight on a dry filament basis of a filament-forming material, such as polyvinyl alcohol polymer and/or a starch polymer, and greater than 20% to about 95% by weight on a dry filament basis of an additive, such as an ingestible active agent, such as a sweetener and/or flavoring agent. The filament may further comprise a plasticizer, such as glycerin and/or pH adjusting agents, such as citric acid.

In still another example of the present invention, the filament of the present invention comprises 0% to less than 20% and/or 0% to less than 15% and/or greater than 0% to less than 15% and/or greater than 0% to less than 12% and/or greater than 2% to less than 10% and/or greater than 4% to less than 8% by weight of water as measured according to the Water Content Test Method described herein. In one example, the filament of the present invention comprises from about 5% to about 10% and/or from about 7% to about 10% by weight of water as measured according to the Water Content Test Method described herein.

In yet another example, the filament of the present invention comprises from about 5% to less than 80% by weight on a dry filament basis of a filament-forming material, such as polyvinyl alcohol polymer and/or a starch polymer, and greater than 20% to about 95% by weight on a dry filament basis of an additive, for example an ingestible active agent, such as a sweetener and/or flavoring agent, wherein the weight ratio of filament-forming material to additive is less than 4.0. The filament may further comprise a plasticizer, such as glycerin and/or pH adjusting agents, such as citric acid.

In yet another example of the present invention, the filaments of the present invention may comprise ingestible active agents that may create health and/or safety concerns if they become airborne. For example, the filament may be used to inhibit enzymes within the filament from becoming airborne.

In one example, the filaments of the present invention may be meltblown filaments. In another example, the filaments of the present invention may be spunbond filaments. In another example, the filaments may be hollow filaments prior to and/or after release of one or more of its active agents.

The filaments of the present invention may be hydrophilic or hydrophobic. The filaments may be surface treated and/or internally treated to change the inherent hydrophilic or hydrophobic properties of the filament.

In one example, the filament exhibits a diameter of less than 100 µm and/or less than 75 µm and/or less than 50 µm and/or less than 25 µM and/or less than 10 µm and/or less than 5 µm and/or less than 1 µm as measured according to the Diameter Test Method described herein. In another example, the filament of the present invention exhibits a diameter of greater than 1 µm as measured according to the Diameter Test Method described herein. The diameter of a filament of the present invention may be used to control the rate of release of one or more active agents present in the filament and/or the rate of loss and/or altering of the filament's physical structure.

The filament may comprise two or more different active agents. In one example, the filament comprises two or more different active agents, wherein the two or more different active agents are compatible or incompatible with one another.

In one example, the filament may comprise an additive within the filament and an additive on an external surface of the filament, such as coating on the filament. Those active agents may be the same or different than the active agents present in the filament. If different, the active agents may be compatible or incompatible with one another.

In one example, one or more active agents may be uniformly distributed or substantially uniformly distributed throughout the filament. In another example, one or more active agents may be distributed as discrete regions within the filament. In still another example, at least one active agent is distributed uniformly or substantially uniformly throughout the filament and at least another active agent is distributed as one or more discrete regions within the filament. In still yet another example, at least one active agent is distributed as one or more discrete regions within the filament and at least another active agent is distributed as one or more discrete regions different from the first discrete regions within the filament.

The filaments may be used as discrete articles. In one example, the filaments may be applied to and/or deposited on a carrier substrate, for example a wipe, paper towel, bath tissue, facial tissue, sanitary napkin, tampon, diaper, adult incontinence article, washcloth, dryer sheet, laundry sheet, laundry bar, dry cleaning sheet, netting, filter paper, fabrics, clothes, undergarments, and the like.

In addition, a plurality of the filaments of the present invention may be collected and pressed into a film.

In one example, a film of the present invention exhibits an average disintegration time per g of sample of less than 55 and/or less than 50 and/or less than 40 and/or less than 30 and/or less than 20 s/g as measured according to the Dissolution Test Method described herein.

In another example, a film of the present invention exhibits an average dissolution time per g of sample of less than 950 and/or less than 900 and/or less than 800 and/or less than 700 and/or less than 600 and/or less than 550 s/g as measured according to the Dissolution Test Method described herein.

In one example, a film of the present invention exhibits a thickness of greater than 0.01 mm and/or greater than 0.05 mm and/or greater than 0.1 mm and/or to about 20 mm and/or to about 10 mm and/or to about 5 mm and/or to about 2 mm and/or to about 0.5 mm and/or to about 0.3 mm as measured by the Thickness Test Method described herein.

Filament-Forming Material

The filament-forming material is any suitable material, such as a polymer or monomers capable of producing a polymer that exhibits properties suitable for making a filament. In one example, the filament-forming material comprises a backbone material as described below.

In one example, the filament-forming material may comprise a polar solvent-soluble material, such as an alcohol-soluble material and/or a water-soluble material.

In another example, the filament-forming material may comprise a non-polar solvent-soluble material.

In still another example, the filament forming material may comprise a polar solvent-soluble material and be free (less than 5% and/or less than 3% and/or less than 1% and/or 0% by weight) of non-polar solvent-soluble materials.

In yet another example, the filament-forming material may be a film-forming material. In still yet another example, the filament-forming material may be synthetic or of natural origin and it may be chemically, enzymatically, and/or physically modified.

In even another example of the present invention, the filament-forming material may comprise a polymer selected from the group consisting of: polymers derived from acrylic monomers such as the ethylenically unsaturated carboxylic monomers and ethylenically unsaturated monomers, polyvinyl alcohol, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethylcelluloses.

In still another example, the filament-forming material may comprises a polymer selected from the group consisting of: polyvinyl alcohol, starch, starch derivatives, cellulose derivatives, hemicellulose, hemicellulose derivatives, proteins, sodium alginate, hydroxypropyl methylcellulose, chitosan, chitosan derivatives, polyethylene glycol, tetramethylene ether glycol, polyvinyl pyrrolidone, hydroxymethyl cellulose, hydroxyethyl cellulose, and mixtures thereof.

In another example, the filament-forming material comprises a polymer is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

Polar Solvent-Soluble Materials

Non-limiting examples of polar solvent-soluble materials include polar solvent-soluble polymers. The polar solvent-soluble polymers may be synthetic or natural original and may be chemically and/or physically modified. In one example, the polar solvent-soluble polymers exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol and/or to about 40,000,000 g/mol and/or to about 30,000,000 g/mol.

In one example, the polar solvent-soluble polymers are selected from the group consisting of: alcohol-soluble polymers, water-soluble polymers and mixtures thereof. Non-limiting examples of water-soluble polymers include water-soluble hydroxyl polymers, water-soluble thermoplastic polymers, water-soluble biodegradable polymers, water-soluble non-biodegradable polymers and mixtures thereof. In one example, the water-soluble polymer comprises polyvinyl alcohol. In another example, the water-soluble polymer comprises starch. In yet another example, the water-soluble polymer comprises polyvinyl alcohol and starch.

a. Water-soluble Hydroxyl Polymers—Non-limiting examples of water-soluble hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof.

In one example, a water-soluble hydroxyl polymer of the present invention is a polysaccharide.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In another example, a water-soluble hydroxyl polymer of the present invention is a non-thermoplastic polymer.

The water-soluble hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol. Higher and lower molecular weight water-soluble hydroxyl polymers may be used in combination with hydroxyl polymers having a certain desired weight average molecular weight.

Well known modifications of water-soluble hydroxyl polymers, such as natural starches, include chemical modifications and/or enzymatic modifications. For example, natural starch can be acid-thinned, hydroxy-ethylated, hydroxy-propylated, and/or oxidized. In addition, the water-soluble hydroxyl polymer may comprise dent corn starch.

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, the present invention is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one example of the present invention, the starch or starch mixture useful in the present invention has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, vinylidene chloride, vinyl chloride, vinyl amine and a variety of acrylate esters.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In one example, the water-soluble hydroxyl polymer is selected from the group consisting of: polyvinyl alcohols, hydroxypropylmethylcelluloses and mixtures thereof. A non-limiting example of a suitable polyvinyl alcohol includes those commercially available from Sekisui Specialty Chemicals America, LLC (Dallas, Tex.) under the CELVOL® trade name. A non-limiting example of a suitable hydroxypropylmethylcellulose includes those commercially available from the Dow Chemical Company (Midland, Mich.) under the METHOCEL® trade name including combinations with above mentioned hydroxypropylmethylcelluloses.

b. Water-soluble Thermoplastic Polymers—Non-limiting examples of suitable water-soluble thermoplastic polymers include thermoplastic starch and/or starch derivatives, polylactic acid, polyhydroxyalkanoate, polycaprolactone, polyesteramides and certain polyesters, and mixtures thereof.

The water-soluble thermoplastic polymers of the present invention may be hydrophilic or hydrophobic. The water-soluble thermoplastic polymers may be surface treated and/or internally treated to change the inherent hydrophilic or hydrophobic properties of the thermoplastic polymer.

The water-soluble thermoplastic polymers may comprise biodegradable polymers.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Backbone Material

The backbone material can comprise any suitable material that exhibits properties suitable for making a filament. Non-limiting examples of backbone materials can include polymers, sugars, sugar alcohols, and combinations thereof.

In one example the filament comprises two or more different backbone materials. In another example the filament comprises three or more different backbone materials. In one example, the polymer can function as a backbone material and in certain examples can also provide a health benefit. In another example, the backbone material comprises a non-thermoplastic material, such as a non-thermoplastic polymer.

The filament can comprise from about 10% to about 80% backbone material, by weight on a dry filament basis, in another example from about 15% to about 75% backbone material, by weight on a dry filament basis, in still another example from about 20% to about 70% backbone material, by weight on a dry filament basis, in another example from about 20% to about 65% backbone material, by weight on a dry filament basis, in still another example from about 25% to about 65%, by weight on a dry filament basis, and in a further example from about 30% to about 60% backbone material, by weight on a dry filament basis.

Each backbone material of the present invention is selected such that its weighted average molecular weight is from about 20,000 Daltons (Da) to about 10,000,000 Da, in an example from about 100,000 Da to about 5,000,000 Da, in yet another example from about 500,000 Da to about 4,000,000 Da, and in still another example from about 1,000,000 Da to about 3,000,000 Da. The weighted average molecular weight is computed by summing the average molecular weights of each backbone material raw material multiplied by their respective relative weight percentages by weight of the total weight of polymers present within the filament.

Polymer

In one example, the backbone material can comprise a polymer. Non-limiting examples of polymers can include naturally sourced polymers, synthetic polymers, and combinations thereof.

Non-limiting examples of naturally sourced polymers can include alginates, gums, protein based polymers, starch based polymers, native starches, modified starches, fiber polymers, other naturally sourced polymers, and combinations thereof.

Non-limiting examples of alginates can include ammonium alginate, calcium alginate, potassium alginate, propylene glycol alginate, and combinations thereof.

Non-limiting examples of gums can include acacia gum, carrageenan, tragacanth gum, guar gum, locust bean gum, xanthan gum, gellan gum, and combinations thereof.

Non-limiting examples of protein based polymers can include whey protein isolate, soy protein isolate, egg albumin, casein, collagen, glutelin, gelatin, gluten, zein, and combinations thereof.

Non-limiting examples of starch based polymers can include cereals, tubers, roots, legumes, fruits, and combinations thereof.

Non-limiting examples of native starches can include can include waxy or high amylase varieties of corn, pea, potato, banana, barley, wheat, rice, sago, amaranth, tapioca, arrowroot, *canna*, sorghum, and combinations thereof.

Non-limiting examples of modified starches can include hydroxypropyl starch, maltodextrin, high amylose starch, and combinations thereof.

Non-limiting examples of fiber polymers can include pectins, fructo-oligosaccharides, inulin, agar, beta-glucans, dextrins, lignin, celluloses, non-starch polysaccharides, reduced starch, polycarbophil, citrus fiber, and combinations thereof.

Non-limiting examples of other naturally sourced polymers can include agar, pullulan, chitin, chitosan, shellac, and combinations thereof.

Non-limiting examples of synthetic polymers can include cellulose derivatives, carbomers, polymethacrylates, other synthetic polymers, and combinations thereof.

Non-limiting examples of cellulose derivatives can include hydroxyethylmethyl cellulose, hydroxylpropylmethyl cellulose, hydroxypropyl cellulose, hydroxypropylethyl cellulose, methylcellulose, hydroxypropyl methylcellulose, and combinations thereof.

Non-limiting examples of carbomers can include carbomer 934, carbomer 934P, carbomer 940, carbomer 94, carbomer 1342, carbomer copolymers, carbomer homopolymers, carbomer interpolymers, and combinations thereof. Some carbomers are available commercially as Carbopol® 934P NF polymer, Carbopol® 971P NF polymer, and Carbopol® 974P NF polymer.

Non-limiting examples of polymethacrylates can include ammonio methacrylate copolymer, basic butylated methacrylate copolymer, methacrylic acid-methyl methacrylate copolymer (1:1), methacrylic acid-ethyl acrylate copolymer (1:1), methacrylic acid-ethyl acrylate copolymer (1:1), methacrylic acid-methyl methacrylate copolymer (1:2), polyacrylate dispersion 30%, methacrylic acid copolymer, amino methacrylate copolymer, ammonio methacrylate copolymer, ammonio methacrylate copolymer dispersion, ethyl acrylate and methyl methacrylate copolymer, and combinations thereof. Some polymethacrylates are available commercially as Eudragit® E 12.5, Eudragit® E 100, Eudragit® E PO, Eudragit® L 12.5 P, Eudragit® L 12.5, Eudragit® L 100, Eudragit® L 100-55, Eudragit® L 30 D-55, Eudragit® S 12.5 P, Eudragit® S 12.5, Eudragit® S 100, Eudragit® FS 30 D, Eudragit® RL 12.5, Eudragit® RL 100, Eudragit® RL PO, Eudragit® RL 30 D, Eudragit® RS 12.5, Eudragit® RS 100, Eudragit® RS PO, Eudragit® RS 30 D, Eudragit® NE 30 D, Eudragit® NE 40 D, Eudragit® NM 30 D, Eastacryl™ 30 D, Kollicoat® MAE 30 DP, Kollicoat® MAE 100 P, Acryl-EZE®, Acryl-EZE® 93 A, and Acryl-EZE® MP.

Non-limiting examples of other synthetic polymers can include polyvinyl alcohol, carboxyvinyl polymers, polyvinyl pyrrolidones, polyethylene oxide, polyoxyethylene, and combinations thereof.

In one example, the polymer of the present invention is selected such that its weighted average molecular weight is from about 20,000 Daltons (Da) to about 10,000,000 Da, in an example from about 100,000 Da to about 5,000,000 Da, in yet another example from about 500,000 Da to about 4,000,000 Da, and in still another example from about 1,000,000 Da to about 3,000,000 Da. The weighted average molecular weight is computed by summing the average molecular weights of each backbone material raw material multiplied by their respective relative weight percentages by weight of the total weight of polymers present within the filament.

In one example, the backbone material is polyvinyl alcohol with a molecular weight from about 10,000 Da to about 250,000 Da, in another example from about 15,000 Da to about 200,000 Da, and in another example from about 20,000 Da to about 150,000 Da.

In one example, the backbone material is selected from the group consisting of alginates, starch based polymers, native starches, modified starches, and combinations thereof with a molecular weight from about 1,000,000 Da to about 6,000,000 Da, in another example from about 1,500,000 Da to about 5,000,000 Da, and in another example from about 2,000,000 Da to about 4,000,000 Da.

In one example, the backbone material is selected from the group consisting of polyvinyl alcohol, pullulan, pectin, corn starch, modified corn starch, hydroxypropyl methylcellulose, and combinations thereof.

Sugars

In one example, the backbone material can be a sugar. Non-limiting examples of sugar can include monosaccharides, disacchairdes, trioses, tetroses, pentoses, hexoses, heptoses, octoses, nonose, sugar alcohols, and combinations thereof.

Non-limiting examples of monosaccharides can include glucose, fructose, and combinations thereof.

Non-limiting examples of disaccharides can include sucrose, maltose, lactose, high fructose corn syrup solids, trehalose, cellobiose, gentiobiose, isomaltose, kojibiose, laminaribiose, mannobiose, melibiose, nigerose, rutinose, xylobiose, lactulose and combinations thereof.

Non-limiting examples of trioses can include glyceraldehydes, dihydroxyacetone, and combinations thereof.

Non-limiting examples of tetroses can include erythrose, threose, erythrulose, and combinations thereof.

Non-limiting examples of pentoses can include arabinose, lyxose, ribose, xylose, ribulose, xylulose, and combinations thereof.

Non-limiting examples of hexoses can include allose, altrose, galactose, glucose, gulose, idose, mannose, talose, fructose, psicose, sorbose, tagatose, and combinations thereof.

Non-limiting examples of heptoses can include mannoheptulose, sedoheptulose, and combinations thereof.

Non-limiting examples of octoses can include octolose, 2-keto-3-deoxy-manno-octonate, and combinations thereof.

A non-limiting example of nonose can include sialose.

Non-limiting examples of sugar alcohols can include sorbitol, manitol, lactitol, isomalt, arabitol, erythritol, glycerol, isomalt, lactitol. maltitol, xylitol, and combinations thereof.

Non-Polar Solvent-Soluble Materials

Non-limiting examples of non-polar solvent-soluble materials include non-polar solvent-soluble polymers. Non-limiting examples of suitable non-polar solvent-soluble materials include cellulose, chitin, chitin derivatives, polyolefins, polyesters, copolymers thereof, and mixtures thereof. Non-limiting examples of polyolefins include polypropylene, polyethylene and mixtures thereof. A non-limiting example of a polyester includes polyethylene terephthalate.

The non-polar solvent-soluble materials may comprise a non-biodegradable polymer such as polypropylene, polyethylene and certain polyesters.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Active Agents

Active agents are a class of additives that are designed and intended to provide a benefit to something other than the filament itself, such as providing a benefit to an environment external to the filament. Active agents may be any suitable additive that produces an intended effect under intended use conditions of the filament. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; hard surface care agents, and/or conditioning agents such as liquid and/or powder dishwashing agents (for hand dishwashing and/or automatic dishwashing machine applications), and polishing agents; other cleaning and/or conditioning agents such as antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, dye transfer-inhibiting agents, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the filament.

For example, if the filament of the present invention is to be used for hair care and/or conditioning then one or more suitable surfactants, such as a lathering surfactant would be selected to provide the desired benefit to a consumer when exposed to conditions of intended use of the filament and/or article incorporating the filament.

In one example, the active agent comprises a non-perfume active agent. In another example, the active agent comprises a non-surfactant active agent.

Surfactants

Non-limiting examples of suitable surfactants include anionic surfactants, cationic surfactants, nonionic surfactants, zwitterionic surfactants, amphoteric surfactants, and mixtures thereof. Co-surfactants may also be included in the filaments. For filaments designed for use as laundry detergents and/or dishwashing detergents, the total level of surfactants should be sufficient to provide cleaning including stain and/or odor removal, and generally ranges from about 0.5% to about 95%. Further, surfactant systems comprising two or more surfactants that are designed for use in filaments for laundry detergents and/or dishwashing detergents may include all-anionic surfactant systems, mixed-type surfactant systems comprising anionic-nonionic surfactant mixtures, or nonionic-cationic surfactant mixtures.

The surfactants herein can be linear or branched. In one example, suitable linear surfactants include those derived from agrochemical oils such as coconut oil, palm kernel oil, soybean oil, or other vegetable-based oils.

a. Anionic Surfactants

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

In one example, anionic surfactants useful in the filaments of the present invention include $C_9$-$C_{15}$ alkyl benzene sulfonates (LAS), $C_8$-$C_{20}$ alkyl ether sulfates, for example alkyl poly(ethoxy) sulfates, $C_8$-$C_{20}$ alkyl sulfates, and mixtures thereof. Other anionic surfactants include methyl ester sulfonates (MES), secondary alkane sulfonates, methyl ester ethoxylates (MEE), sulfonated estolides, and mixtures thereof.

In another example, the anionic surfactant is selected from the group consisting of: $C_{11}$-$C_{18}$ alkyl benzene sulfonates ("LAS") and primary, branched-chain and random $C_{10}$-$C_{20}$ alkyl sulfates ("AS"), $C_{10}$-$C_{18}$ secondary (2,3) alkyl sulfates of the formula $CH_3(CH_2)_x(CHOSO_3^-M^+) CH_3$ and $CH_3(CH_2)_y(CHOSO_3^-M^+) CH_7CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alpha-sulfonated fatty acid esters, the $C_{10}$-$C_{18}$ sulfated alkyl polyglycosides, the $C_{10}$-$C_{18}$ alkyl alkoxy sulfates ("AE$_x$S") wherein x is from 1-30, and $C_{10}$-$C_{18}$ alkyl alkoxy carboxylates, for example comprising 1-5 ethoxy units, mid-chain branched alkyl sulfates as discussed in U.S. Pat. Nos. 6,020,303 and 6,060,443; mid-chain branched alkyl alkoxy sulfates as discussed in U.S. Pat. Nos. 6,008,181 and 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

Other suitable anionic surfactants that may be used are alkyl ester sulfonate surfactants including sulfonated linear esters of $C_8$-$C_{20}$ carboxylic acids (i.e., fatty acids). Other suitable anionic surfactants that may be used include salts of soap, $C_8$-$C_{22}$ primary of secondary alkanesulfonates, $C_8$-$C_{24}$ olefinsulfonates, sulfonated polycarboxylic acids, $C_8$-$C_{24}$ alkylpolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (for example saturated and unsaturated $C_{12}$-$C_{18}$ monoesters) and diesters of sulfosuccinates (for example saturated and unsaturated $C_6$-$C_{12}$ diesters), sulfates of alkylpolysaccharides such as the sulfates of alkylpolyglucoside, and alkyl polyethoxy carboxylates such as those of the formula $RO(CH_2CH_2O)_k$—$CH_2COO$-M+ wherein R is a $C_8$-$C_{22}$ alkyl, k is an integer from 0 to 10, and M is a soluble salt-forming cation.

Other exemplary anionic surfactants are the alkali metal salts of $C_{10}$-$C_{16}$ alkyl benzene sulfonic acids, preferably $C_{11}$-$C_{14}$ alkyl benzene sulfonic acids. In one example, the alkyl group is linear. Such linear alkyl benzene sulfonates are known as "LAS". Such surfactants and their preparation are described for example in U.S. Pat. Nos. 2,220,099 and 2,477,383. IN another example, the linear alkyl benzene sulfonates include the sodium and/or potassium linear straight chain alkylbenzene sulfonates in which the average number of carbon atoms in the alkyl group is from about 11 to 14. Sodium $C_{11}$-$C_{14}$ LAS, e.g., $C_{12}$ LAS, is a specific example of such surfactants.

Another exemplary type of anionic surfactant comprises linear or branched ethoxylated alkyl sulfate surfactants. Such materials, also known as alkyl ether sulfates or alkyl polyethoxylate sulfates, are those which correspond to the formula: R'—O—$(C_2H_4O)_n$—$SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6 and M is sodium. The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the compositions of this invention and used as or in any anionic surfactant component which may be present. Specific examples of non-alkoyxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: R"$OSO_3^-$M+ wherein R" is typically a $C_8$-$C_{20}$ alkyl group, which may be straight chain or branched chain, and M is a water-solubilizing cation. In specific embodiments, R" is a $C_{10}$-$C_{15}$ alkyl group, and M is alkali metal, more specifically R" is $C_{12}$-$C_{14}$ alkyl and M is sodium. Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3)-alkyl sulfates having following formulae:

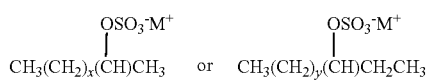

wherein M is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of suitable cations including sodium, potassium, ammonium, and mixtures thereof, and x is an integer of at least 7 and/or at least about 9, and y is an integer of at least 8 and/or at least 9; d) $C_{10}$-$C_{18}$ alkyl alkoxy sulfates (AE$_z$S) wherein z, for example, is from 1-30; e) $C_{10}$-$C_{18}$ alkyl alkoxy carboxylates preferably comprising 1-5 ethoxy units; f) mid-chain branched alkyl sulfates as discussed in U.S. Pat. Nos. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); and j) alpha-olefin sulfonate (AOS).

b. Cationic Surfactants

Non-limiting examples of suitable cationic surfactants include, but are not limited to, those having the formula (I):

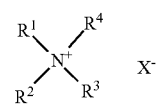

in which $R^1$, $R^2$, $R^3$, and $R^4$ are each independently selected from (a) an aliphatic group of from 1 to 26 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one example, the alkylsulphate radical is methosulfate and/or ethosulfate.

Suitable quaternary ammonium cationic surfactants of general formula (I) may include cetyltrimethylammonium chloride, behenyltrimethylammonium chloride (BTAC), stearyltrimethyl ammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

Non-limiting examples of suitable cationic surfactants are commercially available under the trade names ARQUAD® from Akzo Nobel Surfactants (Chicago, Ill.).

In one example, suitable cationic surfactants include quaternary ammonium surfactants, for example that have up to 26 carbon atoms include: alkoxylate quaternary ammonium (AQA) surfactants as discussed in U.S. Pat. No. 6,136,769; dimethyl hydroxyethyl quaternary ammonium as discussed in 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, for example amido propyldimethyl amine (APA).

Other suitable cationic surfactants include salts of primary, secondary, and tertiary fatty amines. In one embodiment, the alkyl groups of such amines have from about 12 to about 22 carbon atoms, and can be substituted or unsubstituted. These amines are typically used in combination with an acid to provide the cationic species.

The cationic surfactant may include cationic ester surfactants having the formula:

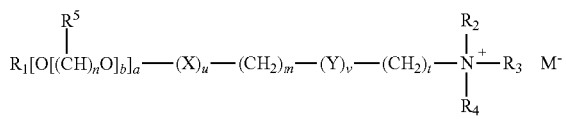

wherein $R_1$ is a $C_5$-$C_{31}$ linear or branched alkyl, alkenyl or alkaryl chain or $M^-.N^+(R_6R_7R_8)(CH_2)_s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R_4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1$-$C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion. In one example, $R_2$, $R_3$ and $R_4$ are independently selected from $CH_3$ and $-CH_2CH_2OH$. In another example, M is selected from the group consisting of halide, methyl sulfate, sulfate, nitrate, chloride, bromide, or iodide.

The cationic surfactants of the present invention may be chosen for use in personal cleansing applications. In one example, such cationic surfactants may be included in the filament and/or fiber at a total level by weight of from about 0.1% to about 10% and/or from about 0.5% to about 8% and/or from about 1% to about 5% and/or from about 1.4% to about 4%, in view of balance among ease-to-rinse feel, rheology and wet conditioning benefits. A variety of cationic surfactants including mono- and di-alkyl chain cationic surfactants can be used in the compositions of the present invention. In one example, the cationic surfactants include mono-alkyl chain cationic surfactants in view of providing desired gel matrix and wet conditioning benefits. The mono-alkyl cationic surfactants are those having one long alkyl chain which has from 12 to 22 carbon atoms and/or from 16 to 22 carbon atoms and/or from 18 to 22 carbon atoms in its alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof. Other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

In one example the cationic ester surfactants are hydrolyzable under the conditions of a laundry wash.

c. Nonionic Surfactants

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like.

In one example, non-limiting examples of nonionic surfactants useful in the present invention include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{72}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. Nos. 6,153,577, 6,020,303 and 6,093,856; alkylpolysaccharides as discussed in U.S. Pat. No. 4,565,647 Llenado, issued Jan. 26, 1986; specifically alkylpolyglycosides as discussed in U.S. Pat. Nos. 4,483,780 and 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Examples of commercially available nonionic surfactants suitable for the present invention include: Tergitol® 15-S-9 (the condensation product of $C_{11}$-$C_{15}$ linear alcohol with 9 moles ethylene oxide) and Tergitol® 24-L-6 NMW (the condensation product of $C_{12}$-$C_{14}$ primary alcohol with 6 moles ethylene oxide with a narrow molecular weight distribution), both marketed by Dow Chemical Company; Neodol® 45-9 (the condensation product of $C_{14}$-$C_{15}$ linear alcohol with 9 moles of ethylene oxide), Neodol® 23-3 (the condensation product of $C_{12}$-$C_{13}$ linear alcohol with 3 moles of ethylene oxide), Neodol® 45-7 (the condensation product of $C_{14}$-$C_{15}$ linear alcohol with 7 moles of ethylene oxide) and Neodol® 45-5 (the condensation product of $C_{14}$-$C_{15}$ linear alcohol with 5 moles of ethylene oxide) marketed by Shell Chemical Company; Kyro® EOB (the condensation product of $C_{13}$-$C_{15}$ alcohol with 9 moles ethylene oxide), marketed by The Procter & Gamble Company; and Genapol LA O3O or O5O (the condensation product of $C_{12}$-$C_{14}$ alcohol with 3 or 5 moles of ethylene oxide) marketed by Hoechst. The nonionic surfactants may exhibit an HLB range of from about 8 to about 17 and/or from about 8 to about 14. Condensates with propylene oxide and/or butylene oxides may also be used.

Non-limiting examples of semi-polar nonionic surfactants useful in the present invention include: water-soluble amine oxides containing one alkyl moiety of from about 10 to about 18 carbon atoms and 2 moieties selected from the group consisting of alkyl moieties and hydroxyalkyl moieties containing from about 1 to about 3 carbon atoms; water-soluble phosphine oxides containing one alkyl moiety of from about 10 to about 18 carbon atoms and 2 moieties selected from the group consisting of alkyl moieties and hydroxyalkyl moieties containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms. See WO 01/32816, U.S. Pat. Nos. 4,681,704, and 4,133,779.

Another class of nonionic surfactants that may be used in the present invention includes polyhydroxy fatty acid amide surfactants of the following formula:

wherein $R^1$ is H, or $C_{1-4}$ hydrocarbyl, 2-hydroxy ethyl, 2-hydroxy propyl or a mixture thereof, $R_2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. In one example, $R^1$ is methyl, $R_2$ is a straight $C_{11-15}$ alkyl or $C_{15-17}$ alkyl or alkenyl chain such as coconut alkyl or mixtures thereof, and Z is derived from a reducing sugar such as glucose, fructose, maltose, lactose, in a reductive amination reaction. Typical examples include the $C_{12}$-$C_{18}$ and $C_{12}$-$C_{14}$ N-methylglucamides.

Alkylpolyaccharide surfactants may also be used as a nonionic surfactant in the present invention.

Polyethylene, polypropylene, and polybutylene oxide condensates of alkyl phenols are also suitable for use as a nonionic surfactant in the present invention. These compounds include the condensation products of alkyl phenols having an alkyl group containing from about 6 to about 14 carbon atoms, in either a straight-chain or branched-chain configuration with the alkylene oxide. Commercially available nonionic surfactants of this type include Igepal CO-630, marketed by the GAF Corporation; and Triton® X-45, X-114, X-100 and X-102, all marketed by the Dow Chemical Company.

Examples of other suitable nonionic surfactants are the commercially-available Pluronic® surfactants, marketed by BASF, the commercially available Tetronic® compounds, marketed by BASF.

d. Zwitterionic Surfactants

Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

e. Amphoteric Surfactants

Non-limiting examples of amphoteric surfactants include: aliphatic derivatives of secondary or tertiary amines, or aliphatic derivatives of heterocyclic secondary and tertiary amines in which the aliphatic radical can be straight- or branched-chain and mixtures thereof. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of amphoteric surfactants.

f. Co-Surfactants

In addition to the surfactants described above, the filaments may also contain co-surfactants. In the case of laundry detergents and/or dishwashing detergents, they typically contain a mixture of surfactant types in order to obtain broad-scale cleaning performance over a variety of soils and stains and under a variety of usage conditions. A wide range of these co-surfactants can be used in the filaments of the present invention. A typical listing of anionic, nonionic, ampholytic and zwitterionic classes, and species of these co-surfactants, is given herein above, and may also be found in U.S. Pat. No. 3,664,961. In other words, the surfactant systems herein may also include one or more co-surfactants selected from nonionic, cationic, anionic, zwitterionic or mixtures thereof. The selection of co-surfactant may be dependent upon the desired benefit. The surfactant system may comprise from 0% to about 10%, or from about 0.1% to about 5%, or from about 1% to about 4% by weight of the composition of other co-surfactant(s).

g. Amine-Neutralized Anionic Surfactants

The anionic surfactants and/or anionic co-surfactants of the present invention may exist in an acid form, which may be neutralized to form a surfactant salt. In one example, the filaments may comprise a surfactant salt form. Typical agents for neutralization include a metal counterion base such as hydroxides, eg, NaOH or KOH. Other agents for neutralizing the anionic surfactants and anionic co-surfactants in their acid forms include ammonia, amines, or alkanolamines. In one example, the neutralizing agent comprises an alkanolamine, for example an alkanolamine selected from the group consisting of: monoethanolamine, diethanolamine, triethanolamine, and other linear or branched alkanolamines known in the art; for example, 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Perfumes

One or more perfume and/or perfume raw materials such as accords and/or notes may be incorporated into one or more of the filaments of the present invention. The perfume may comprise a perfume ingredient selected from the group consisting of: aldehyde perfume ingredients, ketone perfume ingredients, and mixtures thereof.

Bleaching Agents

The filaments of the present invention may comprise one or more bleaching agents. Non-limiting examples of suitable bleaching agents include peroxyacids, perborate, percarbonate, chlorine bleaches, oxygen bleaches, hypohalite bleaches, bleach precursors, bleach activators, hydrogen peroxide, bleach boosters, photobleaches, bleaching enzymes, free radical initiators, peroxygen bleaches, and mixtures thereof.

Enzymes

One or more enzymes may be present in the filaments of the present invention. Non-limiting examples of suitable enzymes include proteases, amylases, lipases, cellulases, carbohydrases including mannanases and endoglucanases, pectinases, hemicellulases, peroxidases, xylanases, phopholipases, esterases, cutinases, keratanases, reductases, oxidases, phenoloxidases, lipoxygenases, ligninases, pullulanases, tannases, penosanases, malanases, glucanases, arabinosidases, hyaluraonidases, chrondroitinases, laccases, and mixtures thereof.

In addition to the enzymes, the filaments may comprise an enzyme stabilizing system, such as calcium and/or magnesium ions.

Dissolution Aids

The filament may incorporate dissolution aids to accelerate dissolution when the filament contains more the 40% surfactant to mitigate formation of insoluble or poorly soluble surfactant aggregates that can sometimes form or surfactant compositions are used in cold water. Non-limiting examples of dissolution aids include sodium chloride, sodium sulfate, potassium chloride, potassium sulfate, magnesium chloride, and magnesium sulfate.

Ingestible Active Agents

The filaments of the present invention may comprise one or more ingestible active agents. In one example, the ingestible active agents may comprise one or more health care active agents.

Health Care Active Agents

In one example, one or more health care actives (health care active agents) may be uniformly distributed or substantially uniformly distributed throughout the filament. In another example, one or more health care actives may be distributed as discrete regions within the filament. In still another example, at least one health care active is distributed uniformly or substantially uniformly throughout the filament and at least another health care active is distributed as one or more discrete regions within the filament. In still yet another example, at least one health care active is distributed as one or more discrete regions within the filament and at least another health care active is distributed as one or more discrete regions different from the first discrete regions within the filament.

The one or more health care actives can include respiratory agents, gastrointestinal agents, central nervous system (CNS) agents, anti-infective agents, nutritional agents, overall wellbeing agents and combinations thereof. The one or more health care actives of the present invention can also be selected from the group consisting of delayed delivery health care actives, extended delivery health care actives, immediate delivery health care actives, targeted delivery health care actives, and combinations thereof. In one example, one or more health care actives are encapsulated. In one example the health care active is selected from the group consisting of dextromethorphan, fexofenadine, famotidine, naproxen, vitamin $B_9$, and combinations thereof.

The personal health care articles of the present invention may also treat one or more health conditions. Non-limiting examples of health conditions can include respiratory conditions, gastrointestinal conditions, CNS conditions, pathogenic infections, nutritional deficiencies, and combinations thereof.

The personal health care articles of the present invention may also provide one or more health benefits. Non-limiting examples of health benefits can include respiratory benefits, gastrointestinal benefits, CNS benefits, anti-infection benefits, nutritional benefits, overall wellbeing benefits, and combinations thereof.

In one example, the health care actives wherein the health care actives comprise particles. The particles of the health care article are less than about 1 μm, in another example the particles are less than about 750 nanometers (nm), in a different example less than about 500 nm, in yet another example less than about 250 nm, in another example less than about 100 nm, in yet another example less than about 50 nm, in another example less than about 25 nm, in another example less than about 10 nm, in another example less than about 5 nm, and in yet another example less than about 1 nm.

All health care actives may be present from about 10% to about 90%, by weight on a dry filament basis, in another example from about 15% to about 80%, by weight on a dry filament basis, in a different example from about 20% to about 75%, by weight on a dry filament basis, in another example from about 25% to about 70%, by weight on a dry filament basis, in a different example from about 30% to about 60%, by weight on a dry filament basis, and in another example from about 35% to about 60%, by weight on a dry filament basis. In another example, the filament comprises greater than about 10%, by weight on a dry filament basis, health care actives, in yet another example greater than about 15%, by weight on a dry filament basis, health care actives, in another example, greater than about 25%, by weight on a dry filament basis, health care actives, in still another example greater than 35%, by weight on a dry filament basis, health care actives, in another example greater than about 40%, by weight on a dry filament basis, health care actives, in another example greater than about 45%, by weight on a dry filament basis, health care actives, an in yet another example greater than about 50%, by weight on a dry filament basis, health care actives.

Respiratory Agents

In an example one or more health care actives can be a respiratory agent. Non-limiting examples of respiratory agents can include nasal decongestants, mucolytics, expectorants, antihistamines, non-narcotic antitussives, demulcents, anesthetics, plant-derived respiratory agents, and combinations thereof. Respiratory agents may be used to treat respiratory conditions. Non-limiting examples of respiratory conditions can include influenza, the common cold, pneumonia, bronchitis, and other viral infections; pneumonia, bronchitis, and other bacterial infections; allergies; sinusitis; rhinitis; and combinations thereof. Respiratory agents may provide a respiratory benefit. Non-limiting examples of respiratory benefits can include treating, respiratory symptoms. Non-limiting examples of respiratory symptoms include nasal congestion, chest congestion, rhinorrhea, coughing, sneezing, headache, body aches, fever, fatigue or malaise, sore throat, difficulty breathing, sinus pressure, sinus pain, and combinations thereof.

Non-limiting examples of decongestants can include phenylephrine, 1-desoxyephedrine, ephedrine, propylhexedrine, pseudoephedrine, phenylpropanolamine, and combinations thereof.

Non-limiting mucolytics can include ambroxol, bromhexine, N-acetylcysteine, and combinations thereof.

Non-limiting expectorants can include guaifenesin, terpin hydrate, and combinations thereof.

Non-limiting examples of antihistamines can include chlorpheniramine, diphenhydramine, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, trani last, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof. In one example, the health care active can be fexofenadine.

Non-limiting examples of antitussives can include benzonatate, chlophedianol, dextromethorphan, levodropropizine, and combinations thereof. In one example the health care active can be dextromethorphan.

Non-limiting examples of demulcents can include glycerin, honey, pectin, gelatin, liquid sugar, and combinations thereof.

Non-limiting examples of anesthetics can include menthol, phenol, benzocaine, lidocaine, hexylresorcinol, and combinations thereof.

Non-limiting examples of plant-derived respiratory agents can include andrographis (*Andrographis paniculata*), garlic (*Album sativum* L.), *Eleutherococcus senticosus*, a guaiacol component (from oils of *cassia* (*Cinnamomum aromaticum*), clove (*Syzygium aromaticum, Eugenia aromaticum, Eugenia caryophyllata*), or cinnamon (*Cinnamomum zeylanicum, Cinnamomum verum, Cinnamomum loureiroi, Cinnamomum camphora, Cinnamomum tamala, Cinnamomum burmannii*)), borage seed oil (*Borago officinalis*), sage (*Salvia officinalis, Salvia lavandulaefolia, Salvia lavandulifolia*), astragalus (*Astragalus membraneceus*), boneset (*Eupatorium perfoliatum*), chamomile (*Matricaria recutita, Chamaemelum nobile*), cordyceps (*Cordyceps sinensis*), echinacea (*Echinacea angustifolia* DC, *Echinacea pallida, Echinacea purpurea*), elder (*Sambucas nigra* L.), *euphorbia*, ginseng (American ginseng, Asian ginseng, Chinese ginseng, Korean red ginseng, *Panax ginseng: Panax* ssp. Including *P. ginseng* C. C. Meyer, and *P. quinquefolius* L.), goldenseal (*Hydrastis canadensis* L.), greater celandine (*Chelidonium majus*), horseradish (*Armoracia rusticana, Cochlearia armoracia*), maitake mushrooms (*Grifola frondosa*) mistletoe (*Visvum album* L.), geranium (*Pelargonium sidoides*), peppermint/peppermint oil (*Menthax peperita* L.), propolis, slippery elm (*Ulmus rubra Muhl, Ulmus fulva Michx*), Sorrel (*Rumex acetosa* L., *Rumex acetosella* L.), thyme/*thymus* extract (*Thymus vulgaris* L.), wild indigo (*Baptisia australis*), quercetin (a flavanol), and combinations thereof.

Gastrointestinal Agents

In one example the one or more health care actives can be a gastrointestinal agent. Non-limiting examples of gastrointestinal agents can include anti-diarrheals, lower gastrointestinal agents, laxatives, anti-emetics, antacids, anti-flattulents, $H_2$ receptor antagonists, proton pump inhibitors, lipase inhibitors, rafting agents, probiotics, prebiotics, dietary fiber, enzymes, plant-derived gastrointestinal agents, anesthetics, and combinations thereof. Gastrointestinal agents may be used to treat gastrointestinal conditions. Non-limiting examples of gastrointestinal conditions can include, gastroesophogeal reflux disease, gastritis, peptic ulcers, dyspepsia, irritable bowel syndrome, colitis, Crohn's disease, Barrett's esophagus, gastrinoma, diarrhea, indigestion, constipation, obesity, pouchitis, diverticulitis, enteritis, enterocolitis, dysphagia, inflamed hemorrhoids, food poisoning and other bacterial infections, influenza and other viral infections, and combinations thereof. Gastrointestinal agents may provide gastrointestinal benefits. Non-limiting examples of gastrointestinal benefits can include restoring digestive balance, treating gastrointestinal symptoms, and combinations thereof. Non-limiting examples of gastrointestinal symptoms can include diarrhea, constipation, upset stomach, vomiting, sour stomach, cramps, gas, bloating, stomach ache, sore throat, difficulty swallowing, unintentional weight loss, visceral hypersensitivity, feeling of fullness, indigestion, nausea, heartburn, urgency to have a bowel movement, lack of appetite, regurgitation, belching, flatulence, blood in stool, dehydration, and combinations thereof.

Non-limiting examples of anti-diarrheals can include loperamide, pharmaceutically acceptable salts of bismuth, attapulgite, activated charcoal, bentonite, and combinations thereof.

Non-limiting examples of lower gastrointestingal agents can include mesalamine, olsalazine sodium, balsalazide disodium, sulfasalazine, tegaserod maleate, and combinations thereof.

Non-limiting examples of laxatives can include bisacodyl, cascara sagrada, castor oil, dietary fiber, resistant starch, resistant maltodextrin, docusate calcium, docusate sodium, lactulose, sennosides, mineral oil, polyethylene glycol 400, polyethylene glycol 3350, and combinations thereof.

Non-limiting examples of anti-emetics can include cyclizine, meclizine, buclizine, dimenhydrinate, scopolamine, trimethobenzamide, dronabinol, 5-$HT_3$ receptor antagonists, aprepitant, and combinations thereof.

Non-limiting examples of antacids can include sodium bicarbonate, sodium carbonate, calcium carbonate, magnesium carbonate, magnesium hydroxide, aluminum hydroxide, magaldrate, and combinations thereof.

Non-limiting examples of anti-atulents can include simethicone.

Non-limiting examples of $H_2$ receptor antagonists can include famotidine, ranitidine, cimetidine, nizatidine, and combinations thereof. In one example, the health care active can be famotidine.

Non-limiting examples of proton pump inhibitors can include omeprazole, lansoprazole, esomeprazole, pantoprazole, rabeprazole, and combinations thereof.

Non-limiting examples of lipase inhibitors can include orlistat.

The filament of the present invention may comprise rafting agents. Non-limiting examples of rafting agents can include alginates, fenugreek, guar gum, xanthan gum, carrageenan, and combinations thereof.

The filament of the present invention may comprise probiotics. Non-limiting examples of probiotics can include microogranisms of the genera *Bacillus, Bacteroides, Bifidobacterium, Enterococcus* (e.g., *Enterococcus faecium*), *Lactobacillus, Leuconostoc, Saccharomyces*, and combinations thereof. In another example of the invention, the probiotic is selected from bacteria of the genera *Bifidobacterium, Lactobacillus*, and combinations thereof.

Non-limiting examples of microorganisms can include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum, Saccharomyces boulardii, Pediococcus cerevisiae, Lactobacillus salivarius, Bacillus coagulans*, and combinations thereof.

Non-limiting examples of prebiotics can include carob bean, citrus pectin, rice bran, locust bean, fructooligosaccharide, oligofructose, galactooligosaccharide, citrus pulp, mannanoligosaccharides, arabinogalactan, lactosucrose, glucomannan, polydextrose, apple pomace, tomato pomace, carrot pomace, *cassia* gum, gum karaya, gum talha, gum arabic, and combinations thereof.

Non-limiting examples of dietary fibers can include, but are not limited to inulin, agar, beta-glucans, chitins, dextrins, lignin, cellulose, modified cellulose, cellulose ethers, hemicelluloses, non-starch polysaccharides, reduced starch, polycarbophil, partially hydrolyzed guar gum, wheat dextrin, and combinations thereof.

In one example, the dietary fiber comprises glucose polymers, preferably those which have branched chains. Among such suitable dietary fibers is one marketed under the tradename "Fibersol2", commercially available from Matsutani Chemical Industry Co., Itami City, Hyogo, Japan.

Other non-limiting examples of suitable dietary fibers can include oligosaccharides, such as inulin and its hydrolysis products commonly known as fructooligosaccharides, galacto-oligosaccharides, xylo-oligosaccharides, oligo derivatives of starch, and combinations thereof.

The dietary fiber can be provided in any suitable form. A non-limiting example is in the form of a plant material which contains the fiber. Non-limiting examples of suitable plant materials can include asparagus, artichoke, onion, wheat, chicory, beet pulp, residues of these plant materials, and combinations thereof.

A non-limiting example of a dietary fiber from such a plant material is inulin extract from extract of chicory. Suitable inulin extracts can be obtained from Orafti SA of Belgium under the trademark Raftiline®. Alternatively the dietary fiber can be in the form of a fructo-oligosaccharide which can be obtained from Orafti SA of Belgium under the trademark Raftilose®. Alternatively, an oliogo-saccharide can be obtained by hydrolyzing inulin, by enzymatic methods, or by using microorganisms as will be understood by those of skill in the art. Alternatively the dietary fiber can be inulin and/or de-sugared inulin available from Cargill Health & Food Technologies, Wayzata, Minn., USA, or from Cosucra SA, Warcoing, Belgium.

In another example, the dietary fiber can be psyllium, available, which can be obtained from The Procter & Gamble Company, Cincinnati, Ohio, under the trademark Metamucil®.

The filament of the present invention can comprise enzymes which can include purified enzymes, partially purified enzymes, extracts containing enzymes, and combinations thereof. Enzymes can be produced synthetically, through genetic modification, or they can be produced naturally by plants, animals, or microorganisms. In some examples the enzymes are produced by plants such as peppermint, pineapple, or papaya. In other examples the enzymes are produced by fungi such as *Aspergillus, Candida, Saccharomyces*, and *Rhizopus*. In another example the enzymes are produced by an animal such as a pig or bovine. In certain examples, the enzymes help support a more complete digestion of food for gastrointestinal health, regularity, and normal bowel function. In other examples, the enzymes can provide wellness benefits or health benefits.

Non-limiting examples of enzymes can include, but are not limited to, proteases, amylases, lipases, and combinations thereof.

Other non-limiting examples of enzymes can include bromelain, pepsin, papain, amyloglucosidase, glucoamylase, malt diastase, maltase, lactase, α-galactosidase, β-glucanase, cellulase, hemilase, hemicellulase, cellulase, xylanase, invertase, pectinase, pancreatin, rennet, phytase, pancrelipase, and combinations thereof.

Non-limiting examples of plant-derived gastrointestinal agents can include materials from the Ginger family (Zigiberaceae), licorice root (*Glycyrrhizin glabra*), marshmallow root (*Althea officinalis, Althea radix*), fennel oil, fennel seed (*Foeniculum vulgare*), caraway oil, caraway seed (*Carum carvi, Carvi fructus, Carvi aetheroleum*), lemon balm (*Melissae folium, Melissa*), horehound herb (*Murrubii herba*), and flaxseed alpha-linoleic acid (*Lini semen*).

Central Nervous System Agents

In one example the one or more health care actives can be a central nervous system (CNS) agent. Non-limiting examples of CNS agents can include sleep aids, nonsteroidal anti-inflammatory drugs, salicylates, opioid analgesics, miscellaneous central nervous system stimulants, anti-emetics, and combinations thereof. Anti-emetics are described herein. CNS agents may be used to treat CNS conditions. Non-limiting examples of CNS conditions can include insomnia, restless leg syndrome, narcolepsy, pain, tobacco dependence, depression, attention deficit disorder, attention deficit hyperactivity disorder, and combinations thereof. Non-limiting examples of pain can include headaches, migraines, arthritis, post-operative pain, dental pain, and combinations thereof. CNS agents may provide CNS benefits. Non-limiting examples of CNS benefits can include increasing alertness, restoring normal circadian rhythm, treating CNS symptoms, and combinations thereof. Non-limiting examples of CNS symptoms can include insomnia, abnormal circadian rhythm, pain, inflammation, fatigue, drowsiness, difficulty concentrating, irritation, vomiting, nausea, and combinations thereof.

The filament of the present invention can comprise sleep aids. Non-limiting examples of sleep aids can include aolpidem, eszopiclone, zaleplon, doxepin, doxylamine, melatonin, ramelteon, estazolam, flurazepam hydrochloride, quazepam, temazepam, triazolam, and combinations thereof.

Non-limiting examples of nonsteroidal anti-inflammatory drugs (NSAIDs) can include acetaminophen, celecoxib, diclofenac, etodolac, fenoprofen calcium, ibuprofen, ketoprofen, mefenamic acid, meloxicam, naproxen, tolmetin sodium, indomethacin, and combinations thereof. In one example, the health care active can be naproxen.

Non-limiting examples of salicylates can include aspirin, magnesium salicylate, salsalate, diflunisal, and combinations thereof.

Non-limiting examples of opioid analgesics can include codeine, hydromorphone hydrochloride, methadone hydrochloride, morphine sulfate, oxycodone hydrochloride, and combinations thereof.

The filament of the present invention can comprise miscellaneous central nervous system stimulants. Non-limiting examples of miscellaneous CNS stimulants can include nicotine, picrotoxin, pentylenetetrazol, and combinations thereof.

Anti-Infective Agents

In one example the one or more health care actives can be an anti-infective agent. Non-limiting examples of anti-infective agents can include antivirals, antimicrobials, and combinations thereof. Anti-infective agents can be used to treat pathogenic infections. Non-limiting examples of pathogenic infections can include tuberculosis, pneumonia, food poisoning, tetanus, typhoid fever, diphtheria, syphilis, meningitis, sepsis, leprosy, whooping cough, lyme disease, gangrene, urinary tract infections, traveler's diarrhea, methicillin-resistant *Staphylococcus aureus* (MRSA), gonorrhea, scarlet fever, cholera, herpes, hepatitis, human immunodeficiency virus (HIV), influenza, measles, mumps, human papillomavirus, polio virus, *giardia*, malaria, tapeworm, roundworm, and combinations thereof. Anti-infective agents may provide anti-infective benefits. Non-limiting examples of anti-infective benefits can include treat pathogenic infection symptoms. Non-limiting examples of pathogenic infection symptoms can include fever, inflammation, nausea, vomiting, loss of appetite, abnormal white blood cell count, diarrhea, rash, skin lesions, sore throat, headache, stomach ache, muscle pain, fatigue, cough, chest pain, difficulty breathing, burning during urination, and combinations thereof.

Non-limiting examples of antivirals can include ganciclovir, valganciclovir, acyclovir, famciclovir, valacyclovir, amantadine, ribavirin, rimantidine HCl, oseltamivir phosphate, adefovir dipivoxil, entecavir, and combinations thereof.

Non-limiting examples of antimicrobials can include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, rifaximi, macrolides, nitrofurantoin, and combinations thereof.

Nutritional Agents

In one example the one or more health care actives can be a nutritional agent. Non-limiting examples of nutritional agents can include vitamins, minerals and electrolytes, dietary fiber, fatty acids, and combinations thereof. Nutritional agents can be used to treat nutritional deficiencies. Non-limiting examples of nutritional deficiencies can include a depressed immune system, birth defects in newborns, heart disease, cancer, Alzheimer's disease, eye diseases, nightblindness, osteoporosis, beriberi, pellagra, scurvy, rickets, alcoholism, irritable bowel syndrome (IBS), low hormone levels, hypertension, and combinations thereof. Nutritional agents may provide a nutritional benefit. Non-limiting examples of nutritional benefits can include disease prevention, lowering cholesterol, increased energy and alertness, preventing aging, restoring digestive balance, and treat nutritional deficiency symptoms and combinations thereof. Non-limiting examples of nutritional deficiency symptoms can include fatigue, muscle weakness, irritability, hair loss, unintentional weight loss, unintentional weight gain, slow wound healing, decreased mental ability, stress, bone fractures, decreased eyesight, decreased rate of wound healing, hyperactivity, dermatitis, muscle cramping, cardiac arrhythmias, depression, and combinations thereof.

Non-limiting examples of vitamins can include vitamin C, vitamin $D_2$ (cholecalciferol), vitamin $D_3$ (ergocalciferol), vitamin A, vitamin $B_1$ (thiamine), vitamin $B_2$ (riboflavin), vitamin $B_3$ (niacin), $B_5$ (pantothenic acid), vitamin $B_6$ (pyridoxine, pyridoxal, or pyridoxamine), vitamin $B_7$ (biotin), vitamin $B_9$ (folic acid), Vitamin $B_{12}$ (cyanocobalmin), vitamin E, and combinations thereof. In one example, the health care active can be vitamin $B_9$.

Non-limiting examples of minerals and electrolytes can include zinc, iron, calcium, iodine, copper, magnesium, potassium, chromium, selenium, and combinations thereof.

Non-limiting examples of antioxidants can include, but are not limited to, polyphenols, superfruits, and combinations thereof.

Non-limiting examples of health care actives containing polyphenols can include tea extract, coffee extract, turmeric extract, grapeseed extract, blueberry extract, and combinations thereof. Nonlimiting examples of superfruits can include açaí, blueberry, cranberry, grape, guarana, mangosteen, noni, pomegranate, seabuckthorn, wolfberry (goji), acerola (Barbados cherry, *Malpighia emarginata, Malpighia glabra*), bayberry (yumberry, *Myrica rubra*), bilberry (*Vaccinium myrtillus*), black raspberry (*Rubus occidentalis*), black chokeberry ("aronia", *Aronia melanocarpa*), blackcurrant (*Ribes nigrum*), camu camu (*Myrciaria dubia*), sour (tart) cherry (*Prunus cerasus*), cupuacu (*Theobroma grandiflorum*), durian (*Durio kutejensis*), elderberry (*Sambucus canadensis, Sambucus nigra*), red guava (*Psidium guajava*, many species), Indian gooseberry (amalaka, amla, *Phyllanthus emblica*), kiwifruit (*Actinidia deliciosa*), lingonberry (*Vaccinium vitis-idaea*), lychee (*Litchi chinensis*), muscadine grape (*Vitis rotundifolia*), papaya (*Carica papaya*), pomelo (*Citrus maxima*), saskatoon berry (*Amelanchier alnifolia*, Nutt), tamarind (*Tamarindus indica*), wild cherry (*Prunus avium*) andyuzu (*Citrus ichangensis, C. reticulata*) and combinations thereof.

Non-limiting examples of fatty acids can include Omega-3 fatty acids, Omega-6 fatty acids, and combinations thereof.

Non-limiting examples of Omega-3 fatty acids can include alpha-linolenic acid, alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, and combinations thereof.

Non-limiting examples of Omega-6 fatty acids can include linoleic acid, gamma-linolenic acid, eicosadienoic acid, dihomo-gamma-linolenic acid, arachidonic acid, docosadienoic acid, adrenic acid, docosapentaenoic acid, and combinations thereof.

Overall Wellbeing Agents

In one example the one or more health care actives can be an overall wellbeing agent. Non-limiting examples of overall wellbeing agents can include energy boosting agents, probiotics, prebiotics, dietary fiber, enzymes, vitamins, minerals and electrolytes, antioxidants, fatty acids, and combinations thereof. Probiotics, prebiotics, dietary fiber, enzymes, vitamins, minerals and electrolyntes, antioxidants, and fatty acids are described herein.

Overall wellbeing agents can be used to provide one or more overall wellbeing benefits. Non-limiting examples of overall wellbeing benefits can include improving and/or maintaining respiratory health, gastrointestinal health, immune health, mobility and joint health, cardiovascular health, skin health, oral/dental health, hair health, eye health, reproductive health including menstrual health, ear, nose and throat health, mental health, energy, normal blood glucose levels, muscle strength, and combinations thereof.

The filament of the present invention can comprise energy boosting agents. Energy boosting actives may provide mammals with more energy or a perception of more energy.

Non-limiting examples of energy boosting agents can include, but are not limited to, caffeine, green and black tea, taurine, *Rhodiola rosea*, Siberian ginseng (*Eleutherococcus senticosus*), CoQ10, L-carnitine, L-Theanine, guarana (*Paullinia cupana*), *Schizandra chinensis, yerba mate* (*Ilex paraguariensis*), goji berry/Wolfberry (*Lycium barbarum* and *L. chinense*), quercetin (a plant-derived flavonol), amalaki/Indian gooseberry (*Phyllanthus emblica*), açaí (from genus *Euterpe*), maca (*Lepidium meyenii*), Ginkgo biloba, glucuronolactone, *panax* ginseng (from species within *Panax*, a genus of 11 species of slow-growing perennial plants with fleshy roots, in the family Araliaceae), *Echinacea* (genus of nine species of herbaceous plants in the Family Asteraceae), rooibos (*Aspalathus linearis*), DHEA, aromas and aromatherapy, noni (*Morinda citrifolia*), mangosteen (*Garcinia mangostana*), and combinations thereof.

Excipients

The filament and/or nonwoven web of the present invention can include one or more excipients. Non-limiting examples of excipients can include filament-forming materials, aesthetic agents, and combinations thereof. Non-limiting examples filament-forming materials can include backbone materials, extensional aids, rheology modifiers, crosslinking agents, and combinations thereof. Non-limiting examples of aesthetic agents can include flavors, colorants, sensates, sweeteners, salivation agents, and combinations thereof.

Aesthetic Agents

The filaments of the present invention may further comprise one or more aesthetic agents.

The one or more aesthetic agents can be selected from the group consisting of flavors, colorants, sensates, sweeteners, salivation agents, and combinations thereof. All aesthetic agents can be present from about 0.001% to about 80%, by weight on a dry filament basis, in another example from about 0.005% to about 60%, by weight on a dry filament basis, in still another example from about 0.05% to about 55%, by weight on a dry filament basis, and in another example from about 0.1% to about 50%, by weight on a dry filament basis. All aesthetic agents can be present from about 0.001% to about 60%, by weight of the article, in another example from about 0.005% to about 50%, by weight of the article, in still another example from about 0.05% to about 40%, by weight of the article, and in another example from about 0.1% to about 35%, by weight of the article.

Flavors

The filament can include one or more flavors. Non-limiting examples of flavors that can be used in the present invention can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, adipic acid, citral, denatonium benzoate, ethyl acetate, ethyl lactate, ethyl maltol, ethylcellulose, fumaric acid, leucine, malic acid, menthol, methionine, monosodium glutamate, sodium acetate, sodium lactate, tartaric acid, thymol, and combinations thereof.

Flavors can be present from about 0.05% to about 50%, by weight of the article, in another example from about 0.01% to about 30%, by weight on a dry filament basis, in still another example from about 0.2% to about 20%, by weight on a dry filament basis, and in another example from about 0.1% to about 15%, by weight on a dry filament basis. Flavors can be present from about 0.05% to about 5%, by weight of the article, in another example from about 0.01% to about 3%, by weight of the article, in still another example from about 0.2% to about 2%, by weight of the article, and in another example from about 0.1% to about 1.5%, by weight of the article.

Colorants

The filament can include one or more colorants. In an example, the colorants provide a visual signal when the filament is exposed to conditions of intended use. Non-limiting examples colorants that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. Colorants can be present from about 0.05% to about 2%, by weight on a dry filament basis or the article, in another example from about 0.01% to about 2%, by weight on a dry filament basis or the article, and in still another example from about 0.02% to about 1.5%, by weight on a dry filament basis or the article.

Sensates

The filaments can include one or more sensates. Non-limiting examples of sensates can include cooling sensates, warming sensates, tingling sensates, and combinations thereof. Sensates are useful to deliver signals to the consumer.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolant P®" by Takasago International., cis & trans p-Menthane-3,8-diols (PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TKIO Coolact (3-1-Menthoxy propane-1,2-diol), Evercool 180 (N-p-benzeneacetonitrile-menthane carboxamide), and combinations thereof. Cooling sensates can be present from about 0.005% to about 60%, by weight on a dry filament basis, in another example from about 0.05% to about 50%, by weight on a dry filament basis, and in still another example from about 0.01% to about 40%, by weight on a dry filament basis. Cooling sensates can be present from about 0.005% to about 10%, by weight of the article, in another example from about 0.05% to about 7%, by weight of the article, and in still another example from about 0.01% to about 5%, by weight of the article.

Non-limiting examples of warming sensates can include TK 1000, TK 1 MM, Heatenol—Sensient Flavors, Optaheat—Symrise Flavors, Cinnamon, Polyethylene glycol, Capsicum, Capsaicin, Curry, FSI Flavors, Isobutavan, Ethanol, Glycerin, Nonivamide 60162807, Hotact VEE, Hotact 1MM, piperine, optaheat 295 832, optaheat 204 656, optaheat 200 349, and combinations thereof. Warming sensates can be present from about 0.005% to about 60%, by weight on a dry filament basis, in another example from about 0.05% to about 50%, by weight on a dry filament basis, and in still another example from about 0.01% to about 40%, by weight on a dry filament basis. Warming sensates can be present from about 0.005% to about 10%, by weight of the article, in another example from about 0.05% to about 7%, by weight of the article, and in still another example from about 0.01% to about 5%, by weight of the article.

Non-limiting examples of tingling sensates can include sichuan pepper, hydroxy alpha sanshool, citric acid, Jambu extracts, spilanthol, and combinations thereof. Tingling sensates can be present from about 0.005% to about 10%, by weight on a dry filament basis or the article, in another example from about 0.01% to about 7%, by weight on a dry filament basis or the article, and in still another example from about 0.015% to about 6%, by weight on a dry filament basis or the article.

Sweeteners

The filament can include one or more sweeteners. Sweeteners can be natural or artificial. Non-limiting examples of sweeteners can include nutritive sweeteners, sugar alcohols, synthetic sweeteners, high intensity natural sweeteners, and combinations thereof. All sweeteners can be present from about 0.05% to about 60%, by weight on a dry filament basis or the article, in another example from about 0.1% to about 50%, by weight on a dry filament basis or the article, in yet another example from about 1% to about 10%, by weight on a dry filament basis or the article.

Non-limiting examples of nutritive sweeteners can include sucrose, dextrose, glucose, fructose, lactose, tagatose, maltose, trehalose, and combinations thereof. Nutritive sweeteners can be present from about 0.1% to about 60%, by weight on a dry filament basis or the article, in another example from about 1% to about 50%, by weight on a dry filament basis or the article, and in a further example from about 0.1% to about 10%, by weight on a dry filament basis or the article.

Non-limiting examples of sugar alcohols can include xylitol, sorbiotl, mannitol, maltitol, lactitol, isomalt, erthritol, and combinations thereof. Sugar alcohols can be present from about 0.1% to about 60%, by weight on a dry filament basis or the article, in another example from about 0.11% to about 50%, by weight on a dry filament basis or the article, and in a further example from about 0.1% to about 10%, by weight on a dry filament basis or the article.

Non-limiting examples of synthetic sweeteners can include aspartame, acesulfame potassium, alitame, sodium saccharin, sucralose, neotame, cyclamate, and combinations thereof. Synthetic sweeteners can be present from about 0.05% to about 10% by weight on a dry filament basis or the article, in another example from about 0.1% to about 5%, by weight on a dry filament basis or the article, and in a further example from about 0.25% to about 4%, by weight on a dry filament basis or the article.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present from about 0.05% to about 10% by weight on a dry filament basis or the article, in another example from about 0.1% to about 5%, by weight on a dry filament basis or the article, and in a further example from about 0.25% to about 4%, by weight on a dry filament basis or the article.

Salivation Agents

The filament can include one or more salivation agents. Non-limiting examples of salivating agents include formula (I):

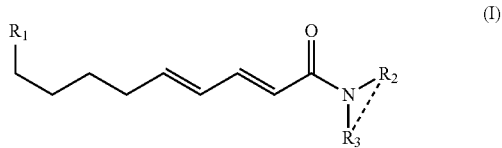

wherein $R_1$ represents C1-C2 n-alkyl; $R_2$ is 2-methyl-1-propyl and $R_3$ is hydrogen, or $R_2$ and $R_3$ taken together is a moiety having the formula —$(CH_2)_n$— wherein n is 4 or 5, and combinations thereof.

In an example, the salivating agent comprises a material wherein $R_2$ is 2-methyl-1-propyl and $R_3$ is hydrogen, more preferably wherein $R_1$ is Cl n-alkyl, $R_2$ is 2-methyl-1-propyl and $R_3$ is hydrogen. More preferably, the salivating agent comprises trans-pellitorin, a chemical having a structure according to formula (II):

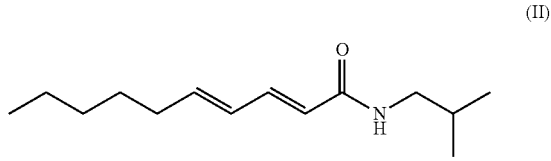 [SMILES: CCCCC/C=C/C=C/C(=O)NCC(C)C]

In another example, the salivation agent could include sodium bicarbonate, sodium chloride, trans pelitorin, and combinations thereof. Salivation agents can be present from about 1% to about 60%, by weight on a dry filament basis, in another example from about 1% to about 50%, by weight on a dry filament basis, and in still another example from about 1% to about 40%, by weight on a dry filament basis. Salivation agents can be present from about 0.005% to about 10%, by weight of the article, in another example from about 0.01% to about 7%, by weight of the article, and in still another example from about 0.015% to about 6%, by weight of the article.

Other Additives

In addition to the active agents described herein, the filaments of the present invention may comprise processing aids and/or materials that provide a signal (visual, audible, smell, feel, taste) that identifies when one or more of the active agents within the filament has been released from the filament.

Filament-Forming Composition

The filaments of the present invention are made from a filament-forming composition. The filament-forming composition is a polar-solvent-based composition. In one example, the filament-forming composition is an aqueous composition comprising one or more filament-forming materials and one or more active agents.

The filament-forming composition of the present invention may have a shear viscosity as measured according to the Shear Viscosity Test Method described herein of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making filaments from the filament-forming composition.

In one example, the filament-forming composition may comprise at least 20% and/or at least 30% and/or at least 40% and/or at least 45% and/or at least 50% to about 90% and/or to about 85% and/or to about 80% and/or to about 75% by weight of one or more filament-forming materials, one or more active agents, and mixtures thereof. The filament-forming composition may comprise from about 10% to about 80% by weight of a polar solvent, such as water.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length per Time),
Area=cross-sectional area of the die exit (units of Length).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In a fiber spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30.

The filament-forming composition of the present invention may have a shear viscosity of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making fibers from the filament-forming composition.

In one example, the non-volatile components of the spinning composition may comprise from about 20% and/or 30% and/or 40% and/or 45% and/or 50% to about 75% and/or 80% and/or 85% and/or 90%. The non-volatile components may be composed of backbone polymers, actives and combinations thereof. The volatile component of the spinning composition will comprise the remaining percentage and range from 10% to 80%.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length³ per Time),
Area=cross-sectional area of the die exit (units of Length).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In a filament spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30.

In one example, the filament-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the filament-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present invention may be added to the filament-forming composition prior to and/or during filament formation and/or may be added to the filament after filament formation. For example, a perfume active agent may be applied to the filament and/or nonwoven web comprising the filament after the filament and/or nonwoven web according to the present invention are formed. In another example, an enzyme active agent may be applied to the filament and/or nonwoven web comprising the filament after the filament and/or nonwoven web according to the present invention are formed. In still another example, one or more particulate active agents, such as one or more ingestible active agents, such as bismuth subsalicylate, which may not be suitable for passing through the spinning process for making the filament, may be applied to the filament and/or nonwoven web comprising the filament after the filament and/or nonwoven web according to the present invention are formed.

Extensional Aids

In one example, the filament comprises an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are preferred in some examples of the invention due to the ability to increase extensional melt viscosity and reducing melt fracture.

The extensional aid, when used in a meltblowing process, is added to the composition of the present invention in an amount effective to visibly reduce the melt fracture and capillary breakage of fibers during the spinning process such that substantially continuous fibers having relatively consistent diameter can be melt spun. Regardless of the process employed to produce filaments, the extensional aids, when used, can be present from about 0.001% to about 10%, by weight on a dry filament basis, in one example, and in another example from about 0.005 to about 5%, by weight on a dry filament basis, in yet another example from about 0.01 to about 1%, by weight on a dry filament basis, and in another example from about 0.05% to about 0.5%, by weight on a dry filament basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include carboxyl modified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Crosslinking Agent

In one example the filament comprises a crosslinking agent that is suitable for crosslinking one or more of the backbone materials. Non-limiting examples of crosslinking agents can include enzymatic crosslinking agents, ionic crosslinking agent, and combinations thereof. Non-limiting examples of ionic crosslinking agents can include calcium carbonate, calcium citrate, calcium citrate malate, calcium chloride, and combinations thereof. In one example, the crosslinking agents can be present from about 0.001% to about 5%, by weight on a dry filament basis, in another example from about 0.005 to about 3%, by weight on a dry filament basis, in yet another example from about 0.01 to about 1%, by weight on a dry filament basis, and in another example from about 0.05% to about 0.5%, by weight on a dry filament basis Release of Active Agent One or more active agents may be released from the filament when the filament is exposed to a triggering condition. In one example, one or more active agents may be released from the filament or a part of the filament when the filament or the part of the filament loses its identity, in other words, loses its physical structure. For example, a filament loses its physical structure when the filament-forming material dissolves, melts or undergoes some other transformative step such that the filament structure is lost. In one example, the one or more active agents are released from the filament when the filament's morphology changes.

In another example, one or more active agents may be released from the filament or a part of the filament when the filament or the part of the filament alters its identity, in other words, alters its physical structure rather than loses its physical structure. For example, a filament alters its physical structure when the filament-forming material swells, shrinks, lenthens, and/or shortens, but retains its filament-forming properties.

In another example, one or more active agents may be released from the filament with the filament's morphology not changing (not losing or altering its physical structure).

In one example, the filament may release an active agent upon the filament being exposed to a triggering condition that results in the release of the active agent, such as by causing the filament to lose or alter its identity as discussed above. Non-limiting examples of triggering conditions include exposing the filament to solvent, a polar solvent, such as alcohol and/or water, and/or a non-polar solvent, which may be sequential, depending upon whether the filament-forming material comprises a polar solvent-soluble material and/or a non-polar solvent-soluble material; exposing the filament to heat, such as to a temperature of greater than 75° F. and/or greater than 100° F. and/or greater than 150° F. and/or greater than 200° F. and/or greater than 212° F.; exposing the filament to cold, such as to a temperature of less than 40° F. and/or less than 32° F. and/or less than 0° F.; exposing the filament to a force, such as a stretching force applied by a consumer using the filament; and/or exposing the filament to a chemical reaction; exposing the filament to a condition that results in a phase change; exposing the filament to a pH change and/or a pressure change and/or temperature change; exposing the filament to one or more chemicals that result in the filament releasing one or more of its active agents; exposing the filament to ultrasonics; exposing the filament to light and/or certain wavelengths; exposing the filament to a different ionic strength; and/or exposing the filament to an active agent released from another filament.

Method for Making Filament

The filaments of the present invention may be made by any suitable process. A non-limiting example of a suitable process for making the filaments is described below.

In one example, a method for making a filament according to the present invention comprises the steps of:

a. providing a filament-forming composition comprising one or more filament-forming materials and one or more ingestible active agents; and b. spinning the filament-forming composition into one or more filaments comprising the one or more filament-forming materials and the one or more active agents that are releasable from the filament when the filament's morphology changes, wherein the total level of the one or more filament-forming materials present in the filament is less than 80% by weight on a dry filament basis and the total level of the one or more active agents present in the filament is greater than 20% by weight on a dry filament basis.

The filament-forming composition may comprise any suitable total level of filament-forming materials and any suitable level of active agents so long as the filament produced from the filament-forming composition comprises a total level of filament-forming materials in the filament of from about 5% to less than 80% by weight on a dry filament basis and a total level of active agents in the filament of greater than 20% to about 95% by weight on a dry filament basis.

In one example, the filament-forming composition may comprise any suitable total level of filament-forming materials and any suitable level of active agents so long as the filament produced from the filament-forming composition comprises a total level of filament-forming materials in the filament of from about 5% to less than 80% by weight on a dry filament basis and a total level of active agents in the filament of greater than 20% to about 95% by weight on a dry filament basis, wherein the weight ratio of filament-forming material to additive is less than 4.0.

In one example, the filament-forming composition comprises from about 1% and/or from about 5% and/or from about 10% to less than 80% and/or less than 65% and/or less than 60% and/or less than 55% and/or less than 50% by weight of the filament-forming composition of filament-forming materials; from about 1% and/or from about 5% and/or from about 10% to about 80% and/or to about 65% and/or to about 60% and/or to about 55% and/or to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more filaments by any suitable spinning process, such as meltblowing and/or spunbonding. In one example, the filament-forming composition is spun into a plurality of filaments by meltblowing. For example, the filament-forming composition may be pumped from an extruder to a melt-blown spinnerette. Upon exiting one or more of the filament-forming holes in the spinnerette, the filament-forming composition is attenuated with air to create one or more filaments. The filaments may then be dried to remove any remaining solvent used for spinning, such as the water.

The filaments of the present invention may be collected on a belt, such as a patterned belt to form a nonwoven web comprising the filaments.

Nonwoven Web

One or more, and/or a plurality of filaments of the present invention may form a nonwoven web. The nonwoven web may be used to deliver the active agents from the filaments of the present invention when the nonwoven web is exposed to conditions of intended use of the filaments and/or nonwoven web.

In one example, the nonwoven web comprises a plurality of identical or substantially identical from a compositional perspective filaments according to the present invention. In another example, the nonwoven web may comprise two or more different filaments according to the present invention. Non-limiting examples of differences in the filaments may be physical differences such as differences in diameter, length, texture, shape, rigidity, elasticity, and the like; chemical differences such as crosslinking level, solubility, melting point, Tg, active agent, filament-forming material, color, level of active agent, level of filament-forming material, presence of any coating on filament, biodegradable or not, hydrophobic or not, contact angle, and the like; differences in whether the filament loses its physical structure when the filament is exposed to conditions of intended use; differences in whether the filament's morphology changes when the filament is exposed to conditions of intended use; and differences in rate at which the filament releases one or more of its active agents when the filament is exposed to conditions of intended use. In one example, two or more filaments within the nonwoven web may comprise the same filament-forming material, but have different active agents. This may be the case where the different active agents may be incompatible with one another, for example an anionic surfactant (such as a shampoo active agent) and a cationic surfactant (such as a hair conditioner active agent).

Figure 4:
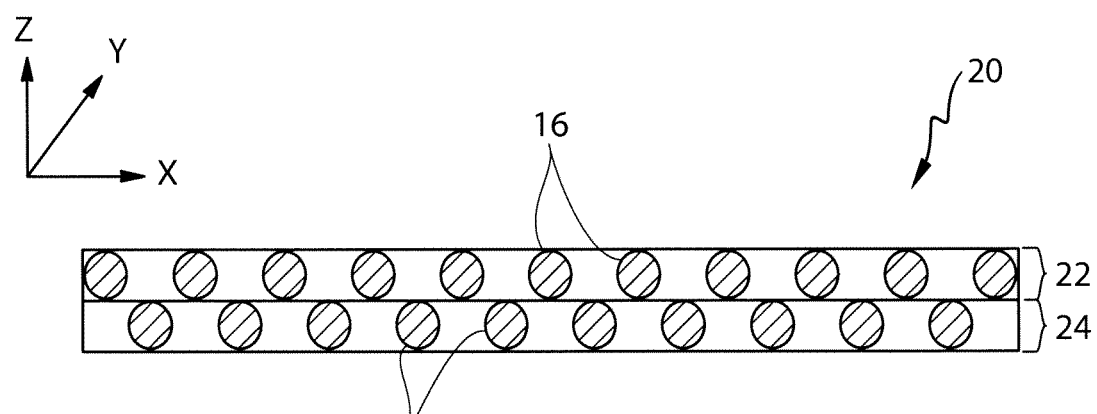
FIG. 4 is a schematic representation of an example of a nonwoven web according to the present invention.

In another example, as shown in FIG. 4, the nonwoven web 20 may comprise two or more different layers 22, 24 (in the z-direction of the nonwoven web 20 of filaments 16 of the present invention that form the nonwoven web 20. The filaments 16 in layer 22 may be the same as or different from the filaments 16 of layer 24. Each layer 22, 24 may comprise a plurality of identical or substantially identical or different filaments. For example, filaments that may release their active agents at a faster rate than others within the nonwoven web may be positioned to an external surface of the nonwoven web.

In another example, the nonwoven web may exhibit different regions, such as different regions of basis weight, density and/or caliper. In yet another example, the nonwoven web may comprise texture on one or more of its surfaces. A surface of the nonwoven web may comprise a pattern, such as a non-random, repeating pattern. The nonwoven web may be embossed with an emboss pattern. In another example, the nonwoven web may comprise apertures. The apertures may be arranged in a non-random, repeating pattern.

In one example, the nonwoven web may comprise discrete regions of filaments that differ from other parts of the nonwoven web.

In one example, the nonwoven web of the present invention exhibits an average disintegration time per g of sample of less than 55 and/or less than 50 and/or less than 40 and/or less than 30 and/or less than 20 s/g as measured according to the Dissolution Test Method described herein.

In another example, the nonwoven web of the present invention exhibits an average dissolution time per g of sample of less than 950 and/or less than 900 and/or less than 800 and/or less than 700 and/or less than 600 and/or less than 550 s/g as measured according to the Dissolution Test Method described herein.

In one example, the nonwoven web of the present invention exhibits a thickness of greater than 0.01 mm and/or greater than 0.05 mm and/or greater than 0.1 mm and/or to about 20 mm and/or to about 10 mm and/or to about 5 mm and/or to about 2 mm and/or to about 0.5 mm and/or to about 0.3 mm as measured by the Thickness Test Method described herein.

Non-limiting examples of uses for the nonwoven web of the present invention include, but are not limited to food, breath freshener, deodorant, wound dressing, medicine delivery, candy substrate, pet food, teeth whitening substrates, adhesive, for example denture adhesive, and other suitable uses of the active agents of the present invention.

The nonwoven web of the present invention may be used as is or may be coated with one or more active agents.

In another example, the nonwoven web of the present invention may be pressed into a film, for example by applying a compressive force and/or heating the nonwoven web to convert the nonwoven web into a film. The film would comprise the active agents that were present in the filaments of the present invention. The nonwoven web may be completely converted into a film or parts of the nonwoven web may remain in the film after partial conversion of the nonwoven web into the film. The films may be used for any suitable purposes that the active agents may be used for including, but not limited to the uses exemplified for the nonwoven web.

Process for Making a Film

The nonwoven web of the present invention may be converted into a film. An example of a process for making a film from a nonwoven web according to the present invention comprises the steps of:

a. providing a nonwoven web comprising a plurality of filaments comprising a filament-forming material, for example a polar solvent-soluble filament-forming material; and b. converting the nonwoven web into a film.

In one example of the present invention, a process for making a film from a nonwoven web comprises the steps of providing a nonwoven web and converting the nonwoven web into a film.

The step of converting the nonwoven web into a film may comprise the step of subjecting the nonwoven web to a force. The force may comprise a compressive force. The compressive force may apply from about 0.2 MPa and/or from about 0.4 MPa and/or from about 1 MPa and/or to about 10 MPa and/or to about 8 MPa and/or to about 6 MPa of pressure to the nonwoven web.

The nonwoven web may be subjected to the force for at least 20 milliseconds and/or at least 50 milliseconds and/or at least 100 milliseconds and/or to about 800 milliseconds and/or to about 600 milliseconds and/or to about 400 milliseconds and/or to about 200 milliseconds. In one example, the nonwoven web is subjected to the force for a time period of from about 400 milliseconds to about 800 milliseconds.

The nonwoven web may be subjected to the force at a temperature of at least 50° C. and/or at least 100° C. and/or at least 140° C. and/or at least 150° C. and/or at least 180° C. and/or to about 200° C. In one example, the nonwoven web is subjected to the force at a temperature of from about 140° C. to about 200° C.

The nonwoven web may be supplied from a roll of nonwoven web. The resulting film may be wound into a roll of film.

Non-Limiting Examples

Figure 5:
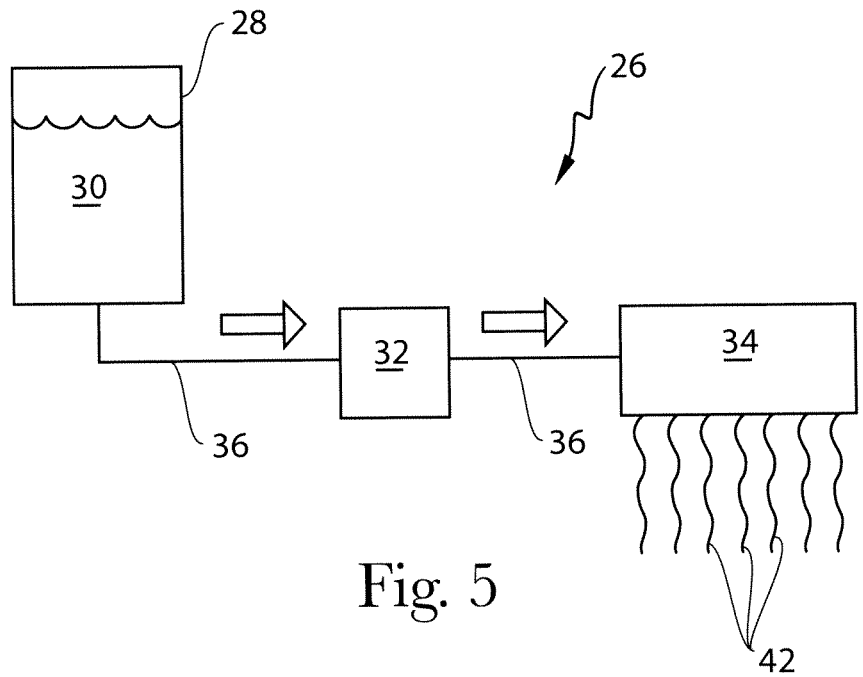
FIG. 5 is a schematic representation of an apparatus suitable for making a filament according to the present invention.
Figure 6:
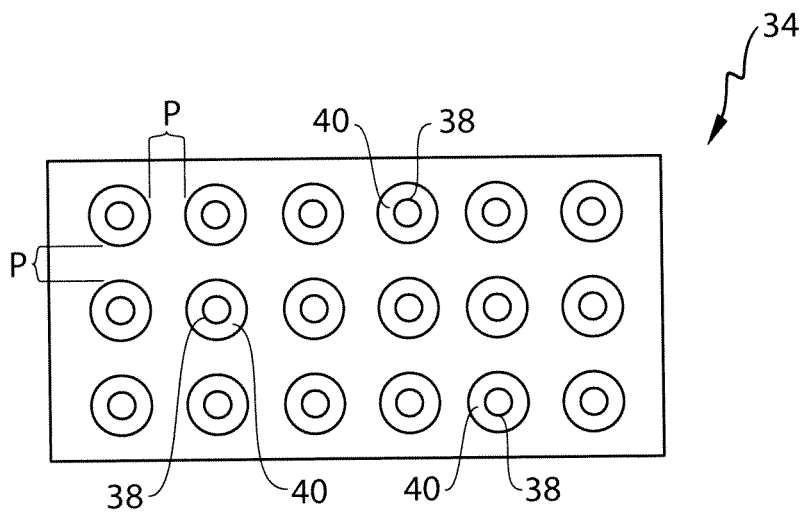
FIG. 6 is a schematic representation of a die suitable for spinning a filament according to the present invention.

Non-limiting examples of filaments according to the present invention are produced by using a small-scale apparatus 26, a schematic representation of which is shown in FIGS. 5 and 6. A pressurized tank 28 suitable for batch operations is filled with a filament-forming composition 30, for example a filament-forming composition that is suitable for making filaments useful as personal health care articles.

The filament-forming compositions described in Examples 1-5 below can be produced into filaments and/or nonwoven webs of the present invention by the following non-limiting process.

A pump 32 (for example a Zenith®, type PEP II pump having a capacity of 5.0 cubic centimeters per revolution (cc/rev), manufactured by Parker Hannifin Corporation, Zenith Pumps division, of Sanford, N.C., USA) is used to pump the filament-forming composition 30 to a die 34. The filament-forming composition's material flow to a die 34 is controlled by adjusting the number of revolutions per minute (rpm) of the pump 32. Pipes 36 are connected the tank 28, the pump 32, and the die 34 in order to transport (as represented by the arrows) the filament-forming composition 30 from the tank 28 to the pump 32 and into the die 34.

The die 34 as shown in FIG. 6 has two or more rows of circular extrusion nozzles 38 spaced from one another at a pitch P of about 1.524 millimeters (about 0.060 inches). The nozzles 38 have individual inner diameters of about 0.305 millimeters (about 0.012 inches) and individual outside diameters of about 0.813 millimeters (about 0.032 inches). Each individual nozzle 38 is encircled by an annular and divergently flared orifice 40 to supply attenuation air to each individual nozzle 38. The filament-forming composition 30 that is extruded through the nozzles 38 is surrounded and attenuated by generally cylindrical, humidified air streams supplied through the orifices 40 encircling the nozzles 38 to produce the filaments 42. Attenuation air is provided by heating compressed air from a source by an electrical-resistance heater, for example, a heater manufactured by Chromalox, Division of Emerson Electric, of Pittsburgh, Pa., USA. An appropriate quantity of steam is added to the attenuation air to saturate or nearly saturate the heated air at the conditions in the electrically heated, thermostatically controlled delivery pipe. Condensate is removed in an electrically heated, thermostatically controlled, separator. The filaments 42 are dried by a drying air stream having a temperature of from about 149° C. (about 300° F.) to about 315° C. (about 600° F.) by an electrical resistance heater (not shown) supplied through drying nozzles (not shown) and discharged at an angle of about 90° relative to the general orientation of the filaments 42 being spun.

The filaments may be collected on a collection device, such as a belt or fabric, in one example a belt or fabric capable of imparting a pattern, for example a non-random repeating pattern to a nonwoven web formed as a result of collecting the filaments on the belt or fabric.

The following non-limiting examples further describe and demonstrate examples within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

The following personal health care article can be prepared in accordance to the present invention:

| Component | Wt % of Processing Mixture |
|---|---|
| Ethylex 2035 Starch[1] | 32.13% |
| Naproxen-Na | 9.64% |
| Distilled Water | q.s. to volume |
| Polyox WSR N-60K PEO[2] | |
| Total | 100% |

[1]Ethylex ™ 2035 Starch available from Tate & Lyle (London, United Kingdom)
[2]Polyox ® WSR N-60K PEO available from Dow (Midland, Michigan)

Example 1 can be made with the following procedure. The distilled water is put into an appropriately sized and cleaned vessel and then is stirred at 100-300 rounds per minute (rpm). The Ethylex™ 2035 and the Polyox® are weighed into a suitable container and are slowly added to the distilled water in small increments using a spatula. The distilled water is continuously stirred and the Ethylex™ 2035 gradually to avoid forming visible lumps and the mixing speed is continuously adjusted to minimize foam formation. Then, the Ethylex™ 2035 and distilled water are gradually heated to 80° C., while continuously being stirred, until the Ethylex™ 2035 is dissolved to form the filament-forming mixture.

The filament-forming mixture is cooled to 25° C., then the naproxen-Na is slowly added to the filament-forming mixture and continuously stirred until the naproxen-Na is dissolved. The filament-forming mixture with the dissolved naproxen-Na is the processing mixture.

This processing mixture is made into filaments using the meltblown process described herein. Then, a nonwoven web are formed by collecting the filaments on a collection device, such as a belt or fabric, such at the nonwoven web exhibits a basis weight of about 600 g/m$^2$ and then cut into personal health care articles with a surface area of about 8 cm$^2$. A mammal in need of a health benefit or a treatment for a health condition, can consume two personal health care articles, containing a total of 220 mg naproxen-Na, by placing the articles directly into his or her mouth, allowing the personal health care article to disintegrate, and then swallowing the disintegrated article.

Example 2

The following personal health care article can be prepared in accordance to the present invention:

| Component | Wt % of Processing Mixture |
|---|---|
| Celvol 523 Polyvinyl Alcohol[3] | 19.56% |
| Doxylamine Succinate | 4.46% |
| FD&C Blue #1 | 0.09% |
| Sucrose | 2.13% |
| Distilled Water | q.s. to volume |
| Total | 100% |

[3]Celvol ® 523 available from Sekisui Corporation (Dallas, Texas)

Example 2 can be made with the following procedure. The distilled water is put into an appropriately sized and cleaned vessel and then is stirred at 100-300 rounds per minute (rpm). The Celvol® 523 is weighed into a suitable container and is slowly added to the distilled water in small increments using a spatula. The distilled water is continuously stirred and Celvol® 523 is added at a speed slow enough to avoid forming visible lumps and the mixing speed is continuously adjusted to minimize foam formation. Then, the Cevol® 523 and distilled water are gradually heated to 80° C., while continuously being stirred, until the Cevlo® is dissolved. The resulting mixture of dissolved Cevol® 523 and distilled water is the filament-forming mixture.

Then, the sucrose and blue #1 are slowly added to the filament-forming mixture. The temperature of the filament-forming mixture with the sucrose and blue #1 is maintained at 80° C. and continuously stirred until the sucrose and blue #1 are dissolved. The filament-forming mixture with sucrose and blue #1 is allowed to cool to 25° C., then the doxylamine succinate is slowly added continuously stirred until the doxylamine succinate is dissolved to form the filament-forming mixture.

This processing mixture is made into filaments using the meltblown process described herein. Then, a nonwoven web are formed by collecting the filaments on a collection device, such as a belt or fabric, such at the nonwoven web exhibits a basis weight of about 92 g/m$^2$ and then cut into personal health care articles with a surface area of about 4 cm$^2$. A mammal in need of a health benefit or a treatment for a health condition, can consume one personal health care article, containing 6.25 mg doxylamine succinate, by placing the articles directly into his or her mouth, allowing the personal health care article to disintegrate, and then swallowing the disintegrated article.

Example 3

The following personal health care article can be prepared in accordance to the present invention:

| Component | Wt % of Processing Mixture |
|---|---|
| Celvol 523 Polyvinyl Alcohol | 12.64% |
| Naproxen-Na | 13.83% |
| Doxylamine Succinate | 0.39% |
| Vanilla | 10.11% |
| Dextromethorphan | 0.94% |
| Propylene Glycol | 10.11% |
| Distilled Water | q.s. to volume |
| Total | 100% |

Example 3 can be made with the following procedure. The propylene glycol is put into an appropriately sized and cleaned vessel and then is stirred at 100-300 rounds per minute (rpm) at 25° C. The dextromethorphan HBr is weighed into a suitable container and is slowly added to the propylene glycol in small increments using a spatula. The propylene glycol and dextromethorphan HBr are stirred continuously at 100-300 rpm at 25° C. until the dextromethorphan HBr dissolves. The propylene glycol/dextromethorphan HBr mixture is set aside.

In a separate vessel, the distilled water is put into an appropriately sized and cleaned vessel and then is stirred at 100-300 rounds per minute (rpm). The Celvol® 523 is weighed into a suitable container and is slowly added to the distilled water in small increments using a spatula while the distilled water is continuously stirred and forming visible lumps is avoided. The mixing speed is adjusted to minimize foam formation. The Celvol® 523, and distilled water are gradually heated to 80° C. while continuously being stirred until the Celvol® 523 is dissolved resulting in the filament-forming mixture.

The filament-forming mixture is allowed to cool to 25° C., then the naproxen-Na, doxylamine succinate, and vanilla are slowly added to the filament-forming mixture and continuously stirred until the naproxen-Na and doxylamine succinate are dissolved and the vanilla is uniformly incorporated. Then, the propylene glycol/dextromethorphan HBr mixture is added to the polyvinyl alcohol, naproxen-Na, doxylamine succinate, and vanilla mixture at 25° C. The two mixtures are continuously stirred until the two mixtures have been uniformly blended to form the processing mixture.

This processing mixture is made into filaments using the meltblown process described herein. Then, a nonwoven web are formed by collecting the filaments on a collection device, such as a belt or fabric, such at the nonwoven web exhibits a basis weight of about 390 g/m² and then cut into personal health care articles with a surface area of about 8 cm². A mammal in need of a health benefit or a treatment for a health condition, can consume two personal health care articles, containing a total of 220 mg naproxen-Na, 6.25 mg doxylamine succinate, and 15 mg dextromethorphan, by placing the articles directly into his or her mouth, allowing the personal health care article to disintegrate, and then swallowing the disintegrated article.

Example 4

The following personal health care article can be prepared in accordance to the present invention:

| Component | Wt % of Processing Mixture |
|---|---|
| Ethylex 2035 Starch | 4.34% |
| Celvol 523 Polyvinyl Alcohol | 12.49% |
| Naproxen-Na | 19.54% |
| Vanilla | 0.54% |
| FD&C blue #1 | 0.11% |
| Sucrose | 1.63% |
| Distilled Water | q.s. to volume |
| Total | 100% |

Example 4 can be made with the following procedure. The distilled water is put into an appropriately sized and cleaned vessel and then is stirred at 100-300 rounds per minute (rpm). The Celvol® 523 is weighed into a suitable container and is slowly added to the distilled water in small increments using a spatula while the distilled water is stirred continuously and forming visible lumps is avoided. The mixing speed is adjusted to minimize foam formation. The Celvol® 523 and distilled water are gradually heated to 80° C. while being stirred continuously until the Celvol® is dissolved. Then, the Ethylex™ 2035 is weighed into a suitable container and is slowly added to the distilled water and Celvol® 523 mixture, in small increments using a spatula while the distilled water and Celvol® 523. The distilled water Celvol® and Ethylex™ is continuously stirred at 80° C. until the Ethylex™ is dissolved. The mixture comprising Celvol®, Ethylex™, and distilled water is the filament-forming mixture.

Then the naproxen-Na, vanilla, blue #1, and sucrose are slowly added to the filament-forming mixture and continuously stirred at 80° C. until the naproxen-Na, vanilla, blue #1, and sucrose are dissolved. The filament-forming mixture with the dissolved naproxen-Na, vanilla, and blue #1 is the processing mixture.

This processing mixture is made into filaments using the meltblown process described herein. Then, a nonwoven web are formed by collecting the filaments on a collection device, such as a belt or fabric, such at the nonwoven web exhibits a basis weight of about 272 g/m² and then cut into personal health care articles with a surface area of about 8 cm². A mammal in need of a health benefit or a treatment for a health condition, can consume two personal health care articles, containing a total of 220 mg naproxen-Na, by placing the articles directly into his or her mouth, allowing the personal health care article to disintegrate, and then swallowing the disintegrated article.

Example 5

The following personal health care article can be prepared in accordance to the present invention:

| Component | Wt % of Processing Mixture |
|---|---|
| Celvol 523 Polyvinyl Alcohol | 13.53% |
| Naproxen-Na | 17.65% |
| Distilled Water | q.s. to volume |
| Total | 100% |

Example 5 can be made with the following procedure. The distilled water is put into an appropriately sized and cleaned vessel and then is stirred at 100-300 rounds per minute (rpm). The Celvol® 523 is weighed into a suitable container and is slowly added to the distilled water in small increments using a spatula. The distilled water is continuously stirred and Celvol® 523 is added at a speed slow enough to avoid forming visible lumps. The mixing speed is continuously adjusted to minimize foam formation. Then, the Cevol® 523 and distilled water are gradually heated to 80° C. while stirred continuously until the Cevlo® is dissolved resulting in the filament-forming mixture.

Then, the filament-forming mixture is allowed to cool to 25° C. and naproxen-Na is slowly added and stirred continuously until the naproxen-Na is dissolved resulting in the processing mixture.

This processing mixture is made into filaments using the meltblown process described herein. Then, a nonwoven web are formed by collecting the filaments on a collection device, such as a belt or fabric, such at the nonwoven web exhibits a basis weight of about 243 g/m² and then cut into personal health care articles with a surface area of about 8 cm². A mammal in need of a health benefit or a treatment for a health condition, can consume two personal health care articles, containing 220 mg of naproxen-Na, by placing the articles directly into his or her mouth, allowing the personal health care article to disintegrate, and then swallowing the disintegrated article. Alternatively two personal health care articles can be placed into 8 ounces of water, stirred until dissolved, and then drank by a mammal in need to deliver 220 mg of naproxen-Na.

Test Methods

Unless otherwise indicated, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 2 hours prior to the test unless otherwise indicated. Samples conditioned as described herein are considered dry samples (such as "dry filaments") for purposes of this invention. Further, all tests are conducted in such conditioned room.

Water Content Test Method

The water (moisture) content present in a filament and/or fiber and/or nonwoven web is measured using the following Water Content Test Method.

A filament and/or nonwoven or portion thereof ("sample") is placed in a conditioned room at a temperature of 73° F.±4° F. (about 23° C.±2.2° C.) and a relative humidity of 50%±10% for at least 24 hours prior to testing. The weight of the sample is recorded when no further weight change is detected for at least a 5 minute period. Record this weight as the "equilibrium weight" of the sample. Next, place the sample in a drying oven for 24 hours at 70° C. with a relative humidity of about 4% to dry the sample. After the 24 hours of drying, immediately weigh the sample. Record this weight as the "dry weight" of the sample. The water (moisture) content of the sample is calculated as follows:

$$\% \text{ Water (moisture) in sample} = 100\% \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample.

Dissolution Test Method

Apparatus and Materials:
- 600 mL Beaker
- Magnetic Stirrer (Labline Model No. 1250 or equivalent)
- Magnetic Stirring Rod (5 cm)
- Thermometer (1 to 100° C.+/−1° C.)
- Template, Stainless Steel (3.8 cm×3.2 cm)
- Timer (0-300 seconds, accurate to the nearest second)
- 35 mm Slide Mount having an open area of 3.8 cm×3.2 cm (commercially available from Polaroid Corporation)
- 35 mm Slide Mount Holder
- City of Cincinnati Water or equivalent having the following properties: Total Hardness=155 mg/L as $CaCO_3$; Calcium content=33.2 mg/L; Magnesium content=17.5 mg/L; Phosphate content=0.0462

Sample Preparation:
1. Cut 3 test samples from a film or a nonwoven web to be tested ("sample") using the template to ensure that the sample fits within the 35 mm slide mount with open area dimensions 24×36 mm (i.e. 3.8 cm×3.2 cm specimen). Cut the samples from areas of the film or nonwoven web equally spaced along the transverse direction of the film or nonwoven web.
2. Lock each of the 3 samples in a separate 35 mm slide mount.
3. Place magnetic stirring rod into the 600 mL Beaker.
4. Obtain 500 mL or greater of Cincinnati city water and measure water temperature with thermometer and, if necessary, adjust the temperature of the water to maintain it at the testing temperature; namely, 5° C. Once the water temperature is at 5° C., fill the 600 mL beaker with 500 mL of the water.
5. Next, place the beaker on the magnetic stirrer. Turn the stirrer on, and adjust stir speed until a vortex develops in the water and the bottom of the vortex is at the 400 mL mark on the 600 mL beaker.
6. Secure the 35 mm slide mount with sample locked therein in a holder designed to lower the 35 mm slide mount into the water in the beaker, for example an alligator clamp of a 35 mm slide mount holder designed to position the 35 mm slide mount into the water present in the 600 mL beaker. The 35 mm slide mount is held by the alligator clamp in the middle of one long end of the 35 mm slide mount such that the long ends of the 35 mm slide mount are parallel to the surface of the water present in the 600 mL beaker. This set up will position the film or nonwoven surface perpendicular to the flow of the water. A slightly modified example of an arrangement of a 35 mm slide mount and slide mount holder are shown in FIGS. 1-3 of U.S. Pat. No. 6,787,512.
7. In one motion, the 35 mm slide mount holder, which positions the 35 mm slide mount above the center of the water in the beaker, is dropped resulting in the 35 mm slide mount becoming submerged in the water sufficiently such that the water contacts the entire exposed surface area of the film or nonwoven sample locked in the 35 mm slide mount. As soon as the water contacts the entire exposed surface area of the film or nonwoven start the timer. Disintegration occurs when the film or nonwoven breaks apart. When all of the visible film or nonwoven is released from the slide mount, raise the 35 mm slide mount out of the water while continuing to monitor the water for undissolved film or nonwoven fragments. Dissolution occurs when all film or nonwoven fragments are no longer visible in the water.
8. Three replicates of each sample are run.
9. Each disintegration and dissolution time is normalized by weight of the sample to obtain values of the disintegration and dissolution times per g of sample tested, which is in units of seconds/gram of sample (s/g). The average disintegration and dissolution times per g of sample tested of the three replicates are recorded.

Diameter Test Method

The diameter of a discrete filament or a filament within a nonwoven web or film is determined by using a Scanning Electron Microscope (SEM) or an Optical Microscope and an image analysis software. A magnification of 200 to 10,000 times is chosen such that the filaments are suitably enlarged for measurement. When using the SEM, the samples are sputtered with gold or a palladium compound to avoid electric charging and vibrations of the filament in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in µm. For filaments within a nonwoven web or film, several filament are randomly selected across the sample of the nonwoven web or film using the SEM or the optical microscope. At least two portions the nonwoven web or film (or web inside a product) are cut and tested in this manner. All together at least 100 such measurements are made and then all data are recorded for statistical analysis. The recorded data are used to calculate average (mean) of the filament diameters, standard deviation of the filament diameters, and median of the filament diameters.

Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. We denote the measured diameter (in µm) of an individual circular filament as di.

In case the filaments have non-circular cross-sections, the measurement of the filament diameter is determined as and set equal to the hydraulic diameter which is four times the cross-sectional area of the filament divided by the perimeter of the cross-section of the filament (outer perimeter in case of hollow filaments). The number-average diameter, alternatively average diameter is calculated as:

$$d_{num} = \frac{\sum_{i=1}^{n} d_i}{n}$$

Thickness Method

Thickness of nonwoven web and/or film is measured by cutting 5 samples of a nonwoven web or film sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in$^2$. The sample is confined between a horizontal flat surface and the load foot loading surface. The load foot loading surface applies a confining pressure to the sample of 15.5 g/cm$^2$. The caliper of each sample is the resulting gap between the flat surface and the load foot loading surface. The caliper is calculated as the average caliper of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Basis Weight Test Method

Basis weight of a fibrous structure sample is measured by selecting twelve (12) individual fibrous structure samples and making two stacks of six individual samples each. If the individual samples are connected to one another vie perforation lines, the perforation lines must be aligned on the same side when stacking the individual samples. A precision cutter is used to cut each stack into exactly 3.5 in.×3.5 in. squares. The two stacks of cut squares are combined to make a basis weight pad of twelve squares thick. The basis weight pad is then weighed on a top loading balance with a minimum resolution of 0.01 g. The top loading balance must be protected from air drafts and other disturbances using a draft shield. Weights are recorded when the readings on the top loading balance become constant. The Basis Weight is calculated as follows:

Basis Weight (lbs/3000 ft$^2$) =

$$\frac{\text{Weight of basis weight pad (g)} \times 3000 \text{ ft}^2}{453.6 \text{ g/lbs} \times 12 \text{ samples} \times [12.25 \text{ in}^2 (\text{Area of basis weight pad})/144 \text{ in}^2]}$$

Basis Weight (g/m$^2$) =

$$\frac{\text{Weight of basis weight pad (g)} \times 10,000 \text{ cm}^2/\text{m}^2}{79.0321 \text{ cm}^2 (\text{Area of basis weight pad}) \times 12 \text{ samples}}$$

Weight Average Molecular Weight

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Filament Composition Test Method

In order to prepare filaments for filament composition measurement, the filaments must be conditioned by removing any coating compositions and/or materials present on the outside surfaces of the filaments that are removable. An example of a method for doing so is washing the filaments 3 times with distilled water. The filaments are then air dried at 73° F.±4° F. (about 23° C.±2.2° C.) until the filaments comprises less than 10% moisture. A chemical analysis of the conditioned filaments is then completed to determine the compositional make-up of the filaments with respect to the filament-forming materials and the active agents and the level of the filament-forming materials and active agents present in the filaments.

The compositional make-up of the filaments with respect to the filament-forming material and the active agents can also be determined by completing a cross-section analysis using TOF-SIMs or SEM. Still another method for determining compositional make-up of the filaments uses a fluorescent dye as a marker. In addition, as always, a manufacturer of filaments should know the compositions of their filaments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples and/or embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web comprising a plurality of inter-entangled filaments and one or more particulate active agents wherein at least one of the one or more particulate active agents is separate from the filaments, wherein the plurality of inter-entangled filaments exhibits lengths greater than or equal to 5.08 cm and comprises one or more filament-forming materials and one or more tooth care active agents that are releasable from the plurality of inter-entangled filaments upon dissolution in water, wherein the total level of the one or more filament-forming materials present in the plurality of inter-entangled filaments is less than 40% by weight on a dry filament basis and the total level of the one or more active agents present in the plurality of inter-entangled filaments is at least 60% by weight on a dry filament basis and wherein the plurality of inter-entangled filaments exhibits diameters of greater than 1 μm as measured according to the Diameter Test Method.

2. The nonwoven web according to claim 1 wherein the total level of the one or more tooth care active agents present in the plurality of inter-entangled filaments is at least 65% by weight on a dry filament basis.

3. The nonwoven web according to claim 1 wherein the one or more filament-forming materials and the one or more tooth care active agents are present in the plurality of inter-entangled filaments at a weight ratio of filament-forming materials to ingestible active agents of less than 4.0.

4. The nonwoven web according to claim 1 wherein the plurality of inter-entangled filaments exhibits a water content of less than 20% as measured according to the Water Content Test Method.

5. The nonwoven web according to claim 1 wherein the one or more filament-forming materials comprises a polar solvent-soluble material.

6. The nonwoven web according to claim 5 wherein the polar solvent-soluble material comprises a water-soluble material.

7. The nonwoven web according to claim 5 wherein the polar solvent-soluble material comprises an alcohol-soluble material.

8. The nonwoven web according to claim 1 wherein the one or more filament-forming materials comprises a non-polar solvent-soluble material.

9. The nonwoven web according to claim 1 wherein the one or more filament-forming materials comprises a sugar.

10. The nonwoven web according to claim 1 wherein the one or more filament-forming materials comprises a polymer.

11. The nonwoven web according to claim 10 wherein the polymer comprises a non-thermoplastic polymer.

12. The nonwoven web according to claim 10 wherein the polymer is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

13. The nonwoven web according to claim 10 wherein the polymer comprises polyvinyl alcohol.

14. The nonwoven web according to claim 10 wherein the polymer comprises starch or starch derivative.

15. The nonwoven web according to claim 10 wherein the polymer exhibits a weight average molecular weight of greater than about 10,000 g/mol.

16. The nonwoven web according to claim 1 wherein the plurality of inter-entangled filaments further comprises a flavoring agent.

17. The nonwoven web according to claim 1 wherein the plurality of inter-entangled filaments further comprises a sweetener.

18. The nonwoven web according to claim 1 wherein the plurality of inter-entangled filaments further comprises a cooling agent.

19. The nonwoven web according to claim 1 wherein the plurality of inter-entangled filaments exhibits diameters of less than 50 μm as measured according to the Diameter Test Method.

20. The nonwoven web according to claim 1 wherein the plurality of inter-entangled filaments comprises two or more different filament-forming materials.

21. The nonwoven web according to claim 1 wherein the plurality of inter-entangled filaments comprises two or more different active agents.

22. The nonwoven web according to claim 1 wherein the plurality of inter-entangled filaments further comprises a coating composition present on an external surface of the plurality of inter-entangled filaments.

23. The nonwoven web according to claim 22 wherein the coating composition comprises one or more active agents.

24. The nonwoven web according to claim 23 wherein at least one of the one or more active agents present in the coating composition is different from at least one of the one or more tooth care active agents present in the plurality of inter-entangled filaments.

25. A film produced from the nonwoven web according to claim 1.

26. The nonwoven web according to claim 1 wherein the plurality of inter-entangled filaments exhibits a water content of from 0% to about 20% as measured according to the Water Content Test Method.

27. The nonwoven web according to claim 26 wherein the plurality of inter-entangled filaments exhibits a water content of greater than 0% to less than 15% as measured according to the Water Content Test Method.

* * * * *